(12) United States Patent
Baker, Jr. et al.

(10) Patent No.: US 8,175,665 B2
(45) Date of Patent: May 8, 2012

(54) METHOD AND APPARATUS FOR SPECTROSCOPIC TISSUE ANALYTE MEASUREMENT

(75) Inventors: Clark R. Baker, Jr., Newman, CA (US);
Nicholas J. Durr, Austin, TX (US);
Murtaza Mogri, Stanford, CA (US);
Carine Hoarau, Lafayette, CA (US);
Rafael Ostrowski, Pittsburg, CA (US);
Martin P. Debreczeny, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1458 days.

(21) Appl. No.: 11/716,482

(22) Filed: Mar. 9, 2007

(65) Prior Publication Data
US 2008/0221412 A1 Sep. 11, 2008

(51) Int. Cl.
*A61B 5/1455* (2006.01)
(52) U.S. Cl. .................................... 600/310; 600/322
(58) Field of Classification Search .................. 600/310, 600/322, 331, 336, 340, 473, 475; 356/39; 250/339.12
See application file for complete search history.

(56) References Cited

U.S. PATENT DOCUMENTS

| | | | |
|---|---|---|---|
| 3,998,550 A | 12/1976 | Konishi et al. | |
| 4,066,068 A | 1/1978 | Nilsson et al. | |
| 4,364,008 A | 12/1982 | Jacques | |
| 4,711,244 A | 12/1987 | Kuzara | |
| 4,723,554 A | 2/1988 | Oman et al. | |
| 4,805,623 A | 2/1989 | Jobsis | |
| 4,850,365 A | 7/1989 | Rosenthal | |
| 4,860,753 A | 8/1989 | Amerena | |
| 4,883,055 A | 11/1989 | Merrick | |
| 4,907,594 A | 3/1990 | Muz | |
| 5,057,695 A | 10/1991 | Hirao et al. | |
| 5,086,781 A | 2/1992 | Bookspan | |
| 5,111,817 A | 5/1992 | Clark et al. | |
| 5,146,091 A | 9/1992 | Knudson | |
| 5,224,478 A | 7/1993 | Sakai et al. | |

(Continued)

FOREIGN PATENT DOCUMENTS

CA 2353007 A1 6/2000

(Continued)

OTHER PUBLICATIONS

U.S. Appl. No. 11/528,154, filed Sep. 27, 2006, Debreczeny et al.

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

Methods and systems for calculating body fluid metrics are provided. In accordance with an exemplary embodiment of the present technique, there is provided a method for calculating body fluid metrics by acquiring an absorbance spectrum of a subject's tissue over a range of near-infrared light, performing a multi-linear regression of the absorbance spectrum of the subject's tissue in relation to absorbance spectra of tissue constituents, and calculating body fluid metrics based on the results of the multi-linear regression. A system is provided having a sensor for emitting the light into the subject's tissue and detecting reflected, scattered, or transmitted light, a spectrometer for processing the detected light and generating the absorbance spectrum of the subject's tissue, memory for storing absorbance spectra of the tissue constituents and a multi-linear regression model, and a processor for performing the multi-linear regression and calculating the body fluid metrics.

51 Claims, 13 Drawing Sheets

U.S. PATENT DOCUMENTS

| | | | |
|---|---|---|---|
| 5,277,181 A | 1/1994 | Mendelson et al. | |
| 5,279,295 A | 1/1994 | Martens et al. | |
| 5,282,467 A | 2/1994 | Piantadosi et al. | |
| 5,309,907 A * | 5/1994 | Fang et al. | 600/342 |
| 5,337,745 A | 8/1994 | Benaron | |
| 5,337,937 A | 8/1994 | Remiszewski et al. | |
| 5,348,004 A | 9/1994 | Hollub | |
| 5,353,790 A * | 10/1994 | Jacques et al. | 600/473 |
| 5,355,880 A | 10/1994 | Thomas et al. | |
| 5,377,674 A | 1/1995 | Kuestner | |
| 5,440,388 A * | 8/1995 | Erickson | 356/456 |
| 5,499,627 A | 3/1996 | Steuer et al. | |
| 5,615,689 A | 4/1997 | Kotler | |
| 5,638,816 A * | 6/1997 | Kiani-Azarbayjany et al. | 600/316 |
| 5,687,721 A | 11/1997 | Kuhls | |
| 5,701,902 A | 12/1997 | Vari et al. | |
| 5,720,284 A | 2/1998 | Aoyagi et al. | |
| 5,729,333 A * | 3/1998 | Osten et al. | 356/39 |
| 5,735,284 A | 4/1998 | Tsoglin et al. | |
| 5,747,789 A | 5/1998 | Godik | |
| 5,755,672 A | 5/1998 | Arai et al. | |
| 5,788,643 A | 8/1998 | Feldman | |
| 5,803,908 A | 9/1998 | Steuer et al. | |
| 5,827,181 A | 10/1998 | Dias et al. | |
| 5,833,602 A | 11/1998 | Osemwota | |
| 5,853,364 A | 12/1998 | Baker, Jr. et al. | |
| 5,860,919 A | 1/1999 | Kiani-Azarbayjany et al. | |
| 5,906,582 A | 5/1999 | Kondo et al. | |
| 6,064,898 A | 5/2000 | Aldrich | |
| 6,125,297 A | 9/2000 | Siconolfi | |
| 6,149,591 A | 11/2000 | Henderson et al. | |
| 6,178,342 B1 | 1/2001 | Thompson et al. | |
| 6,222,189 B1 | 4/2001 | Misner et al. | |
| 6,246,894 B1 | 6/2001 | Steuer et al. | |
| 6,280,396 B1 | 8/2001 | Clark et al. | |
| 6,336,044 B1 | 1/2002 | Ghiassi et al. | |
| 6,370,426 B1 | 4/2002 | Campbell et al. | |
| 6,400,971 B1 | 6/2002 | Finarov et al. | |
| 6,402,690 B1 | 6/2002 | Rhee et al. | |
| 6,442,408 B1 * | 8/2002 | Wenzel et al. | 600/310 |
| 6,456,870 B1 * | 9/2002 | Rennert et al. | 600/310 |
| 6,466,807 B1 | 10/2002 | Dobson et al. | |
| 6,488,677 B1 | 12/2002 | Bowman et al. | |
| 6,512,936 B1 | 1/2003 | Monfre et al. | |
| 6,591,122 B2 | 7/2003 | Schmitt | |
| 6,592,574 B1 | 7/2003 | Shimmick et al. | |
| 6,600,946 B1 | 7/2003 | Rice | |
| 6,606,509 B2 | 8/2003 | Schmitt | |
| 6,615,064 B1 | 9/2003 | Aldrich | |
| 6,635,491 B1 | 10/2003 | Khalil et al. | |
| 6,636,759 B2 | 10/2003 | Robinson | |
| 6,643,543 B2 | 11/2003 | Takehara et al. | |
| 6,654,620 B2 | 11/2003 | Wu et al. | |
| 6,668,181 B2 | 12/2003 | Wenzel et al. | |
| 6,675,029 B2 | 1/2004 | Monfre et al. | |
| 6,687,519 B2 | 2/2004 | Steuer et al. | |
| 6,777,240 B2 | 8/2004 | Hazen et al. | |
| 6,849,046 B1 | 2/2005 | Eyal-Bickels | |
| 6,873,865 B2 | 3/2005 | Steuer et al. | |
| 6,882,874 B2 | 4/2005 | Huiku | |
| 6,898,451 B2 * | 5/2005 | Wuori | 600/322 |
| 6,950,699 B1 | 9/2005 | Manwaring et al. | |
| 6,961,598 B2 | 11/2005 | Diab et al. | |
| 7,027,849 B2 | 4/2006 | Al-Ali | |
| 7,142,901 B2 | 11/2006 | Kiani et al. | |
| 7,206,621 B2 | 4/2007 | Aoyagi et al. | |
| 7,215,984 B2 | 5/2007 | Diab et al. | |
| 7,215,986 B2 | 5/2007 | Diab et al. | |
| 7,215,991 B2 | 5/2007 | Besson et al. | |
| 7,221,970 B2 | 5/2007 | Parker | |
| 7,236,811 B2 | 6/2007 | Schmitt | |
| 7,236,813 B2 | 6/2007 | Parker | |
| 7,239,902 B2 | 7/2007 | Schmitt et al. | |
| 7,257,433 B2 | 8/2007 | Takamura et al. | |
| 7,277,741 B2 | 10/2007 | Debreczeny et al. | |
| 7,283,242 B2 | 10/2007 | Thornton | |
| 7,328,053 B1 | 2/2008 | Diab et al. | |
| 7,343,186 B2 | 3/2008 | Lamego et al. | |
| 7,376,453 B1 | 5/2008 | Diab et al. | |
| 7,383,070 B2 | 6/2008 | Diab et al. | |
| 7,392,075 B2 | 6/2008 | Baker, Jr. | |
| 7,430,444 B2 | 9/2008 | Pologe | |
| 2001/0020122 A1 | 9/2001 | Steuer et al. | |
| 2001/0041829 A1 * | 11/2001 | Thennadil et al. | 600/322 |
| 2003/0060693 A1 | 3/2003 | Monfre et al. | |
| 2003/0109998 A1 | 6/2003 | Lorenz et al. | |
| 2004/0127777 A1 | 7/2004 | Ruchti et al. | |
| 2004/0147034 A1 | 7/2004 | Gore et al. | |
| 2004/0230106 A1 * | 11/2004 | Schmitt et al. | 600/310 |
| 2005/0070773 A1 | 3/2005 | Chin et al. | |
| 2005/0119538 A1 | 6/2005 | Jeon et al. | |
| 2005/0131286 A1 | 6/2005 | Parker et al. | |
| 2005/0168722 A1 | 8/2005 | Forstner et al. | |
| 2005/0192488 A1 | 9/2005 | Bryenton et al. | |
| 2005/0192493 A1 | 9/2005 | Wuori | |
| 2005/0209517 A1 | 9/2005 | Diab et al. | |
| 2005/0250998 A1 | 11/2005 | Huiku | |
| 2005/0267346 A1 | 12/2005 | Faber et al. | |
| 2006/0020181 A1 | 1/2006 | Schmitt | |
| 2006/0030763 A1 | 2/2006 | Mannheimer et al. | |
| 2006/0030764 A1 | 2/2006 | Porges et al. | |
| 2006/0052680 A1 | 3/2006 | Diab et al. | |
| 2006/0084864 A1 | 4/2006 | Schmitt et al. | |
| 2006/0122475 A1 | 6/2006 | Balberg et al. | |
| 2006/0129037 A1 | 6/2006 | Kaufman et al. | |
| 2006/0129038 A1 | 6/2006 | Zelenchuk et al. | |
| 2006/0167350 A1 | 7/2006 | Monfre et al. | |
| 2006/0189861 A1 | 8/2006 | Chen et al. | |
| 2006/0200014 A1 | 9/2006 | Fine et al. | |
| 2006/0200016 A1 | 9/2006 | Diab et al. | |
| 2006/0217609 A1 | 9/2006 | Diab et al. | |
| 2006/0247506 A1 | 11/2006 | Balberg et al. | |
| 2006/0253016 A1 | 11/2006 | Baker, Jr. et al. | |
| 2006/0276696 A1 | 12/2006 | Schurman | |
| 2006/0287587 A1 | 12/2006 | Yarita | |
| 2006/0287588 A1 | 12/2006 | Yarita | |
| 2007/0032707 A1 | 2/2007 | Coakley et al. | |
| 2007/0032709 A1 | 2/2007 | Coakley et al. | |
| 2007/0032710 A1 | 2/2007 | Raridan et al. | |
| 2007/0032711 A1 | 2/2007 | Coakley et al. | |
| 2007/0032712 A1 | 2/2007 | Raridan et al. | |
| 2007/0032713 A1 | 2/2007 | Eghbal et al. | |
| 2007/0032716 A1 | 2/2007 | Raridan et al. | |
| 2007/0073122 A1 | 3/2007 | Hoarau | |
| 2007/0073123 A1 | 3/2007 | Raridan, Jr. | |
| 2007/0073125 A1 | 3/2007 | Hoarau et al. | |
| 2007/0073126 A1 | 3/2007 | Raridan, Jr. | |
| 2007/0073127 A1 | 3/2007 | Kiani et al. | |
| 2007/0073128 A1 | 3/2007 | Hoarau et al. | |
| 2007/0078309 A1 | 4/2007 | Matlock et al. | |
| 2007/0078311 A1 | 4/2007 | Al-Ali et al. | |
| 2007/0106137 A1 | 5/2007 | Baker, Jr. et al. | |
| 2007/0118027 A1 | 5/2007 | Baker, Jr. et al. | |
| 2007/0129614 A1 | 6/2007 | Schmitt et al. | |
| 2007/0167693 A1 | 7/2007 | Scholler et al. | |
| 2007/0225581 A1 | 9/2007 | Diab et al. | |
| 2007/0244376 A1 | 10/2007 | Wang | |
| 2007/0249918 A1 | 10/2007 | Diab et al. | |
| 2007/0260129 A1 | 11/2007 | Chin | |
| 2007/0260130 A1 | 11/2007 | Chin | |
| 2007/0260131 A1 | 11/2007 | Chin | |
| 2007/0282178 A1 | 12/2007 | Scholler et al. | |
| 2007/0282183 A1 | 12/2007 | Scholler et al. | |
| 2007/0291832 A1 | 12/2007 | Diab et al. | |
| 2008/0004513 A1 | 1/2008 | Walker et al. | |
| 2008/0004514 A1 | 1/2008 | Diab et al. | |
| 2008/0033266 A1 | 2/2008 | Diab et al. | |
| 2008/0036752 A1 | 2/2008 | Diab et al. | |
| 2008/0045823 A1 | 2/2008 | Diab et al. | |
| 2008/0058622 A1 | 3/2008 | Baker | |
| 2008/0076980 A1 | 3/2008 | Hoarau | |
| 2008/0076981 A1 | 3/2008 | Hoarau | |
| 2008/0076994 A1 | 3/2008 | Hoarau | |
| 2008/0076995 A1 | 3/2008 | Hoarau | |
| 2008/0076996 A1 | 3/2008 | Hoarau | |

| | | | |
|---|---|---|---|
| 2008/0081969 | A1 | 4/2008 | Feldman et al. |
| 2008/0097173 | A1 | 4/2008 | Soyemi et al. |
| 2008/0154104 | A1 | 6/2008 | Lamego et al. |
| 2008/0208019 | A1 | 8/2008 | Nitzan |
| 2008/0255436 | A1 | 10/2008 | Baker |

FOREIGN PATENT DOCUMENTS

| | | | |
|---|---|---|---|
| DE | 19855521 A1 | 6/2000 | |
| EP | 1135184 A1 | 6/2000 | |
| EP | 1184663 A2 | 3/2002 | |
| EP | 1491135 | 12/2004 | |
| FR | 2710517 | 4/1995 | |
| JP | 4-40940 | 2/1992 | |
| JP | 5-329163 | 12/1993 | |
| JP | 11-244266 | 9/1999 | |
| JP | 2004 081427 A | 3/2004 | |
| JP | 25095606 | 4/2005 | |
| JP | 25169020 | 6/2005 | |
| JP | 25278758 | 10/2005 | |
| JP | 26075354 | 3/2006 | |
| WO | WO 93/13706 A2 | 7/1993 | |
| WO | WO 95/19562 A | 7/1995 | |
| WO | WO 98/34097 | 8/1998 | |
| WO | WO 00/32262 A1 | 6/2000 | |
| WO | WO 00/71025 A1 | 11/2000 | |
| WO | WO 01/16577 A1 | 3/2001 | |
| WO | WO 03/010510 A | 2/2003 | |
| WO | WO 2005/041765 A | 5/2005 | |
| WO | WO2006097910 | 9/2006 | |
| WO | WO 2006107947 A | 10/2006 | |
| WO | WO2006124455 | 11/2006 | |

OTHER PUBLICATIONS

U.S. Appl. No. 11/528,218, filed Sep. 27, 2006, Campbell, et al.
U.S. Appl. No. 11/529,024, filed Sep. 28, 2006, Agashe, et al.
U.S. Appl. No. 11/541,010, filed Sep. 29, 2006, Baker, Jr., et al.
U.S. Appl. No. 11/716,260, filed Mar. 9, 2007, Hoarau.
U.S. Appl. No. 11/716,264, filed Mar. 9, 2007, Campbell, et al.
U.S. Appl. No. 11/716,394, filed Mar. 9, 2007, Koh, et al.
U.S. Appl. No. 11/716,443, filed Mar. 9, 2007, Hausmann, et al.
U.S. Appl. No. 11/716,481, filed Mar. 9, 2007, Baker, Jr.
U.S. Appl. No. 11/716,482, filed Mar. 9, 2007, Baker, Jr., et al.
U.S. Appl. No. 11/716,776, filed Mar. 9, 2007, Baker, Jr.
U.S. Appl. No. 11/716,777, filed Mar. 9, 2007, Baker, Jr.
U.S. Appl. No. 11/716,778, filed Mar. 9, 2007, Baker, Jr.
U.S. Appl. No. 11/901,643, filed Sep. 18, 2007, Debreczeny et al.
Wheeler, Owen H., "Near Infrared Spectra of Organic Compounds," Department of Chemistry, College of Agriculture and Mechanic Arts, University of Puerto Rico (Mar. 1929).
Pace, Nello, et al., "Studies on Body Composition: III. The body water and chemically combined nitrogen content in relation to fat content," Naval Medical Research Institute, Bethesda, Maryland (Jan. 11, 1945).
Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).
Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).
Forbes, R.M., et al., "The Composition of the Adult Human Body as Determined by Chemical Analysis," Division of Animal Nutrition, and the Department of Anatomy, University of Illinois, Jan. 19, 1953.
Buijs, K., et al., "Near-Infrared Studies of the Structure of Water. I. Pure Water," *The Journal of Chemical Physics*, vol. 39, No. 8, pp. 2035-2041 (Oct. 15, 1963).
Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).
Goldstein, R., et al., "The Near-Infrared Absorption of Liquid Water at Temperatures Between 27 and 209° C.," *J. Quant. Spectrosc. Radiat Transfer.*, vol. 4, pp. 441-451 (1964).

Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).
Houseman, R.A., et al., "The measurement of total body water in living pigs by deuterium oxide dilution and its relation to body composition," *Br. J. Nutr.*, vol. 30, pp. 149-156 (1973).
Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).
Lesser, G.T., et al., "Body water compartments with human aging using fat-free mass as the reference standard," *Am J. Physiol Regul Integr Comp Physiol.*, vol. 236, pp. 215-220 (1979).
Sheng, Hwai-Ping, et al., "A review of body composition studies with emphasis on total body water and fat," *The American Journal of Clinical Nutrition*, vol. 32., pp. 630-647 (Mar. 1979).
Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).
Fomon, Samuel J., et al., "Body composition of reference children from birth to age 10 years," The American Journal of clinical Nutrition, vol. 35, pp. 1169-1175, (May 1982).
Lanza, Elaine, "Determination of Moisture, Protein, Fat, and Calories in Raw Pork and Beef by near Infrared Spectroscopy," *Journal of Food Science*, vol. 48, pp. 471-474 (1983).
Shields, R. G., Jr., et al., "Efficacy of Deuterium Oxide to Estimate Body Composition of Growing Swine"; *Journal of Animal Science*, vol. 57, No. 1, pp. 66-73, (1983).
Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).
Cohn, S.H., et al., "Assessment of cellular mass and lean body mass by noninvasive nuclear techniques," *J. Lab Clin Med.*, vol. 105, pp. 305-311 (1985).
Hannon, John P., et al., "Splenic red cell sequestration and blood vol. measurements in conscious pigs," *Am J. Physiol.*, vol. 248, pp. R293-R301 (1985).
Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).
Cox, Patrick, et al., "Variations in Lipids in Different Layers of Porcine Epidermis," *J. Invest Dermatol.*, vol. 87, pp. 741-744 (1986).
Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).
Hedberg, Chrisopher L., et al., "The Time Course of Lipid Biosynthesis in Pig Epidermis," *J. Invest Dermatol.*, vol. 91, pp. 169-174 (1988).
Hedberg, Christopher L., et al., "The nonpolar Lipids of Pig Epidermis," *J. Invest Dermatol.*, vol. 90, pp. 225-229 (1988).
Trapp, Scott A., et al., "An improved spectrophotometric bromide assay for the estimation of extracellular water volume," *Clinica Chimica Acta.*, vol. 181, pp. 207-212, (1989).
Bommannan, D., et al., "Examination of Stratum Comeum Barrier Function In Vivo by Infrared Spectroscopy," *J. Invest Dermatol*, vol. 95, pp. 403-408 (1990).
Hannon, John P., et al., "Normal pHysiological Values for Conscious Pigs Used in Biomedical Research," *Laboratory Animal Science*, vol. 40, No. 3, May 1990.
Mak, Vivien H.W., et al., "Oleic Acid Concentration and Effect in Human Stratum Corneum: Non-Invasive determination by Attenuated Total Reflectance Infrared Spectroscopy In Vivo," *Journal of Controlled Release*, vol. 12, pp. 67-75 (1990).
Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Drummer, C., et al., "Effects of an acute saline infusion on fluid and electrolyte metabolism in humans," *Am J. Physiol.*, vol. 262, pp. F744-F754 (1992).

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E., et al., "Near infrared calibrations for goat's milk components; protein, total casein, $\alpha_s$-, $\beta$- and $\kappa$-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol. Meas.*, 14:455-461 (1993).

Bewig, Karen M., et al., "Discriminant Analysis of Vegetable Oils by Near-Infrared Reflectance Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J., et al., "Absolute quantification of deoxyhaemoglobin concentration in tissue near infrared spectroscopy," *Phys. Med. Biol.*, vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-72.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N.J., et al.; "In vitro multifrequency electrical impedance measurements and modeling of the cervix in late pregnancy", *Physiological Measurement*, vol. 17, pp. A97-A103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water," *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "Perspectives—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M-380 (2001).

Divert, Victor E., "Body Thermal State Influence on Local Skin Thermosensitivity," *International Journal of Circumpolar Health*, vol. 60, pp. 305-311 (2001).

Du, Y., et al., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch—Eur J. Physiol*, vol. 442, pp. 362-368 (2001).

Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Kamba, Masayuki, et al., "Proton magnetic resonance spectroscopy for assessment of human body composition," *Am J. Clin. Nutr.*, vol. 73, pp. 172-176 (2001).

Lever, M., et al., "Some ways of looking at compensatory kosmotropes and different water environments," *Comparative Biochemistry and Physiolog.*, vol. 130, Part A, pp. 471-486, (2001).

Mingrone, G., et al., "Unreliable use of standard muscle hydration value in obesity," *Am J. Physiol Endocrinal Metab.*, vol. 280, pp. E365-E371, (2001).

Ritz, Patrick, "Chronic Cellular Dehydration in the Aged Patient," Journal of Gerontology, vol. 56A, No. 6, pp. M349-M352 (2001).

Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P., et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-bum period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Tsukahara, K., et al., "Dermal fluid translocation is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogeneous group of adult humans," *Eur J. Appl. Physiol.*, vol. 85, pp. 326-332 (2001).

Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).

Watson, Walter, "Hydration of fat-free body mass: new physiological modeling approach," *Am J. Physiol. Endocrinol. Metab.*, Letters to the Editor, vol. 278, pp. E752-E753 (2001).

Attas, E. Michael, et al., "Near-IR Spectroscopic Imaging for Skin Hydration: The Long and the Short of it," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Blank, T.B., et al., "Clinical Results from a Non-Invasive Blood Glucose Monitor," *Photonics West 2002 Meeting*, San Jose, California, Jan. 19-25, 2002 (25 pages).

Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma Volume Expanders," *Anesthesiology*, vol. 96, No. 6, pp. 1371-1380 (Jun. 2002).

Endo, Yutaka, et al., "Changes in Blood Pressure and Muscle Sympathetic Nerve Activity during Water Drinking in Humans," *Japanese Journal of Physiology*, vol. 52, pp. 421-427 (2002).

Haga, Henning A., et al., "Motor responses to stimulation during isoflurane anaesthesia in pigs," *Veterinary Anaesthesia and Analgesia*, vol. 29, pp. 69-75 (2002).

Klaus, Stephan, et al., "Assessment of fluid balance by measurement of skin tissue thickness during clinical anaesthesia, " *Clin. Physiol. & Func. Im.*, vol. 22, pp. 197-201 (2002).

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria, et al., "Charactrization of Reconstructed Skin Models," *Skin Pharmacol Appl Skin Physiol.*, vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am J. Clin Nutr.*, vol. 76, pp. 384-389 (2002).

Baković, Darija, et al., "Spleen volume and blood flow response to repeated breath-hold apneas," *J. Appl. Physiol.*, vol. 95, pp. 1460-1466 (2003).

Bartok, Cynthia, et al., "Measurement of nutritional statusin simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum Corneum at Different Hydration Levels," *J. Invest. Dermatol*, vol. 150, pp. 750-758 (2003).

Butte, Nancy F., et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of Trauma, Injury Infection, and Critical Care*, vol. 54, No. 5, pp. S20-S25 (May Supplement 2003).

Cook, Lynda S., "IV Vluid Resuscitation," *Journal of Infusion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: issues for the 21$^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol. Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Mentes, Janet C., et al., "Reducing Hydration=-Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjä L., et al., "Dielectric constant of skin and subcutaneous fat to assess fluid changes after cardiac surgery", *Physiological Measurement*, 24: 3383-390, 2003.

Rhodes, Andrew, et al., "Book Report—Haemodynamic monitoring in critically ill patients," *Critical Care*, vol. 8, p. 203 (2004).

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Robinson, Martin P., et al., "A novel method of studying total body water content using a resonant cavity: experiments and numerical simulation," *Phys. Med. Biol.*, vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab*, vol. 284, pp. E267-E273 (2003).

Windberger, U, et al., "Whole blood viscosity, plasma viscosity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *Physiol. Meas.*, vol. 25, pp. 447-454, (2004).

St-Onge, Marie-Pierre, et al., "Dual-energy X-ray absorptiometry lean soft tissue hydration: independent contributions of intra-and extracellular water," *Am J. Physiol. Endocrinol Metab*, vol. 287, pp. E842-E847, Jul. 6, 2004.

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last accessed, Nov. 30, 2005).

Haroun, D., et al., "Composition of the fat-free mass in obese and nonobese children: matched case—control analyses," *International Journal of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mitedu/ProoressReports/HomeAutomation/Report2-5/Chapter04.pdf (last accessed, Nov. 30, 2005).

Garcia-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

U.S. Appl. No. 61/009,681, filed Dec. 31, 2007, Bloom, et al.

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

International Search Report PCT/US2008/003014, 4 pages, mailed Sep. 23, 2008.

* cited by examiner

METHOD AND APPARATUS FOR SPECTROSCOPIC TISSUE ANALYTE MEASUREMENT

BACKGROUND OF THE INVENTION

1. Field of the Invention

The present invention relates to medical methods and systems, and more particularly to methods and systems for estimating body fluid metrics.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

The maintenance of body fluid balance is of foremost concern in the care and treatment of critically ill patients, yet physicians have access to few diagnostic tools to assist them in this vital task. Patients with congestive heart failure, for example, frequently suffer from chronic systemic edema which must be controlled within tight limits to ensure adequate tissue perfusion and prevent dangerous electrolyte disturbances. Conversely, dehydration from diarrhea is one of the most common causes of hospitalization of infants and children and can be life-threatening if not recognized and treated promptly. Additionally, hospital admission of long-term care patients due to dehydration occurs with alarming frequency, high costs to the health care system, and frequently with poor outcomes for patients.

The most common method for judging the severity of edema or dehydration is based on the interpretation of subjective clinical signs (e.g., swelling of limbs, dry mucous membranes), with additional information provided by measurements of the frequency of urination, heart rate, serum urea nitrogen (SUN) to creatinine ratios, and blood electrolyte levels. However, none of these variables alone is a direct and quantitative measure of water retention or loss.

An indicator dilution technique, which provides the most accurate direct measure of water in body tissues, is the present de facto standard for assessment of body fluid distribution. However, indicators can take up to four hours to equilibrate in an adult, and require careful collection of fluid samples and extensive equipment for precise analysis, making the technique inconvenient for a clinical setting.

Alternatively, a great deal of research has been conducted regarding an electrical impedance technique, which involves the use of electrical impedance monitors for measurement of total body water. This electrical-impedance technique is based on measuring changes in the high-frequency (typically 10 KHz-1 MHz) electrical impedance of a portion of the body. However, while results of using the electrical-impedance technique for a single tissue have proven to be clinically useful, mixed results have been obtained with the electrical-impedance technique in clinical studies of whole body fluid disturbances, as reported by various investigators. The results generally indicate that the electrical-impedance technique can be inaccurate when measuring total body water. The rather poor accuracy of the technique seen in many studies points to unresolved deficiencies when applied in a clinical setting.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a method for calculating one or more body fluid metrics, including acquiring an absorbance spectrum of a subject's tissue at a range of wavelengths of light, determining concentrations of a plurality of constituents of the subject's tissue by performing a multi-linear regression of the absorbance spectrum in relation to a plurality of absorbance spectra of the constituents, and calculating one or more body fluid metrics based on the concentrations.

There is further provided a method for calculating one or more body fluid metrics, including measuring an intensity spectrum of a subject's tissue, processing the intensity spectrum to determine an absorbance spectrum of the tissue, performing a multi-linear regression of the absorbance spectrum in relation to a plurality of analyte absorbance spectra, wherein the analytes are representative of tissue constituents, and determining concentrations of the tissue constituents based on the multi-linear regression.

There is further provided a system for calculating one or more body fluid metrics, including a sensor configured to emit a range of wavelengths of light into a subject's tissue and to detect reflected, scattered, or transmitted light, a spectrometer configured to process the reflected, scattered, or transmitted light and to generate an absorbance spectrum of the subject's tissue across the range of wavelengths of light, a memory configured to store a plurality of absorbance spectra of tissue constituents across the range of wavelengths of light and to store a multi-linear regression model, and a processor configured to perform a multi-linear regression of the absorbance spectrum of the subject's tissue with respect to the plurality of absorbance spectra of tissue constituents based on the multi-linear regression model and to calculate one or more body fluid metrics based on the multi-linear regression.

There is further provided one or more tangible, machine-readable media, having code executable to perform the acts of performing a multi-linear regression of an absorbance spectrum of a subject's tissue in relation to a plurality of absorbance spectra of skin constituents and calculating one or more body fluid metrics based on the multi-linear regression.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with present embodiments, a monitor may be used to non-invasively measure a relative quantity of a specific constituent in a subject's skin. For example, the monitor may be used to measure the percentage of water in the subject's tissue. To obtain such measurements, the monitor may be configured to use near-infrared (NIR) diffuse reflectance spectroscopy to measure the absorbance of water relative to other major tissue constituents. Specifically, the monitor may shine light into the subject's tissue and then measure an intensity of the light after it has been reflected, scattered, and/or transmitted by the tissue. By shining a wide-band light into a patient's tissue, a spectrum of the tissue absorbance over a range of light wavelengths may be measured or observed. In accordance with embodiments of the present invention, once the wide-band absorbance spectrum is measured, it may be utilized as essentially a weighted combination of the absorbance spectra of the tissue's constituents (e.g., water, fat, and proteins). Accordingly, the concentration of each of the constituents in the tissue may be determined by performing a multi-linear regression of the tissue absorbance spectrum using individual absorbance spectra of the tissue constituents. Further, based on the relative concentrations of the tissue constituents, one or more body fluid metrics may be calculated.

One body fluid metric which may be desirable to determine in a clinical setting is a patient's body water percentage. However, studies have shown that the fraction of total water in a human body varies significantly (e.g., varying from 44-58%) with age and gender. Such variations can create issues with the proper interpretation of total body water percentage measurements.

Figure 1:
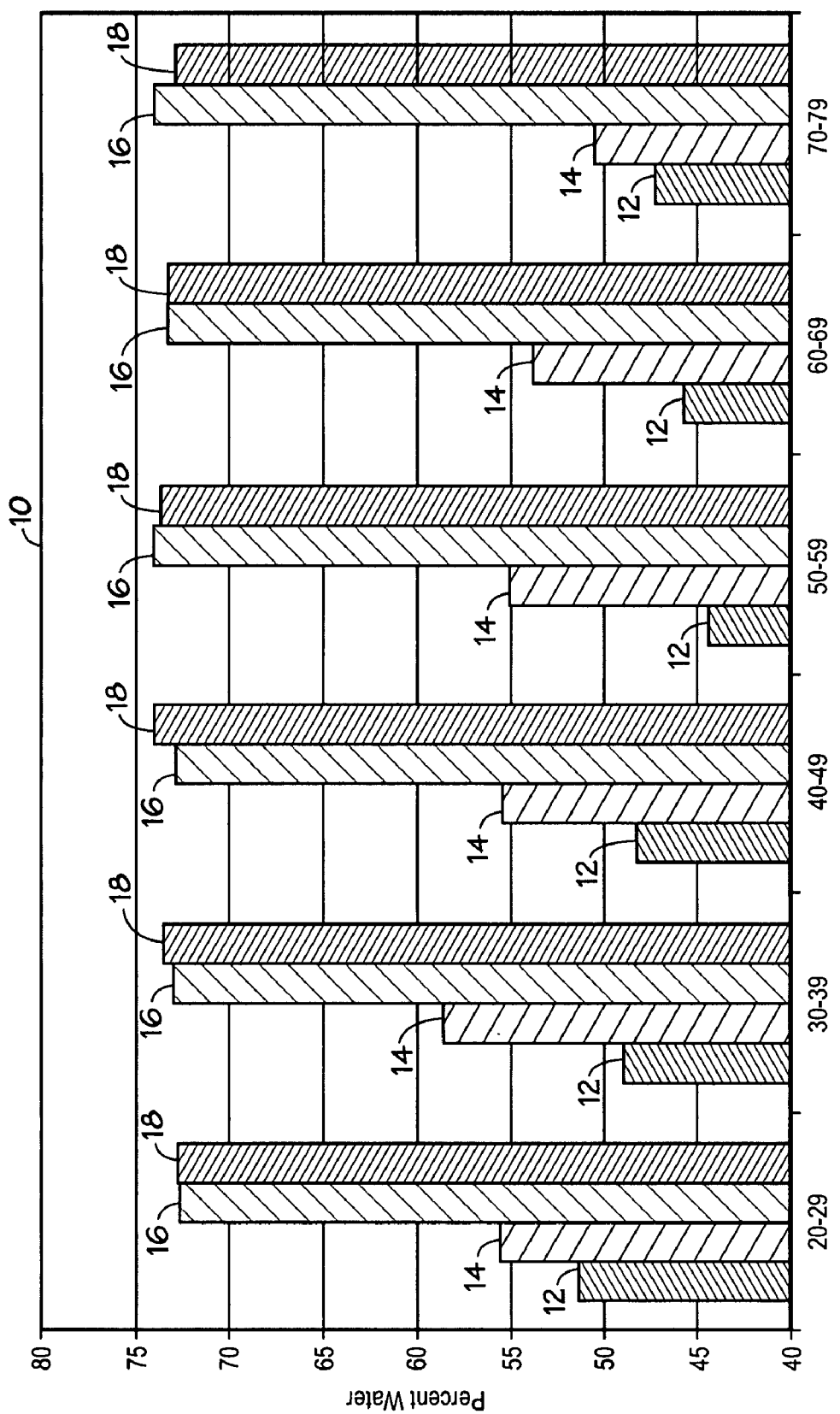
FIG. 1 is a bar graph of body water percentage in men and women across varying age groups as observed in accordance with an exemplary embodiment of the present invention.

FIG. 1 includes a bar graph 10 that summarizes an exemplary study of the total water in a human body. According to the study results illustrated by bar graph 10, the percentage of water per total body weight in human females 12 is lower on average than the percentage of water per total body weight for human males 14 in the same age groups. The observed difference between genders is because lean tissue, such as muscle, is composed mostly of water, while fatty tissue contains relatively little water. Women have a higher proportion of body fat, therefore female bodies on average have a lower percentage of water per total body weight. However, when fat is excluded from the percent water calculation, a measurement of percentage water in lean tissue can be obtained. The fraction of water in lean tissue in healthy subjects is consistent across both gender and age (e.g., varying from 73-74%). In other words, the percentage water per lean body mass 16 in females is not significantly different from the percentage water per lean body mass 18 in males. This lean tissue water content may be referred to as the "hydration index" (HI). It is now recognized that the HI of skin is a good predictor for total body HI. This relationship between skin and total body HI is described in U.S. Pat. App. No. 60/857,045, entitled "METHOD AND APPARATUS FOR ACCESSING LOCAL AND WHOLE BODY HYDRATION," filed Nov. 6, 2006, which is herein incorporated by reference in its entirety for all purposes.

Figure 2:
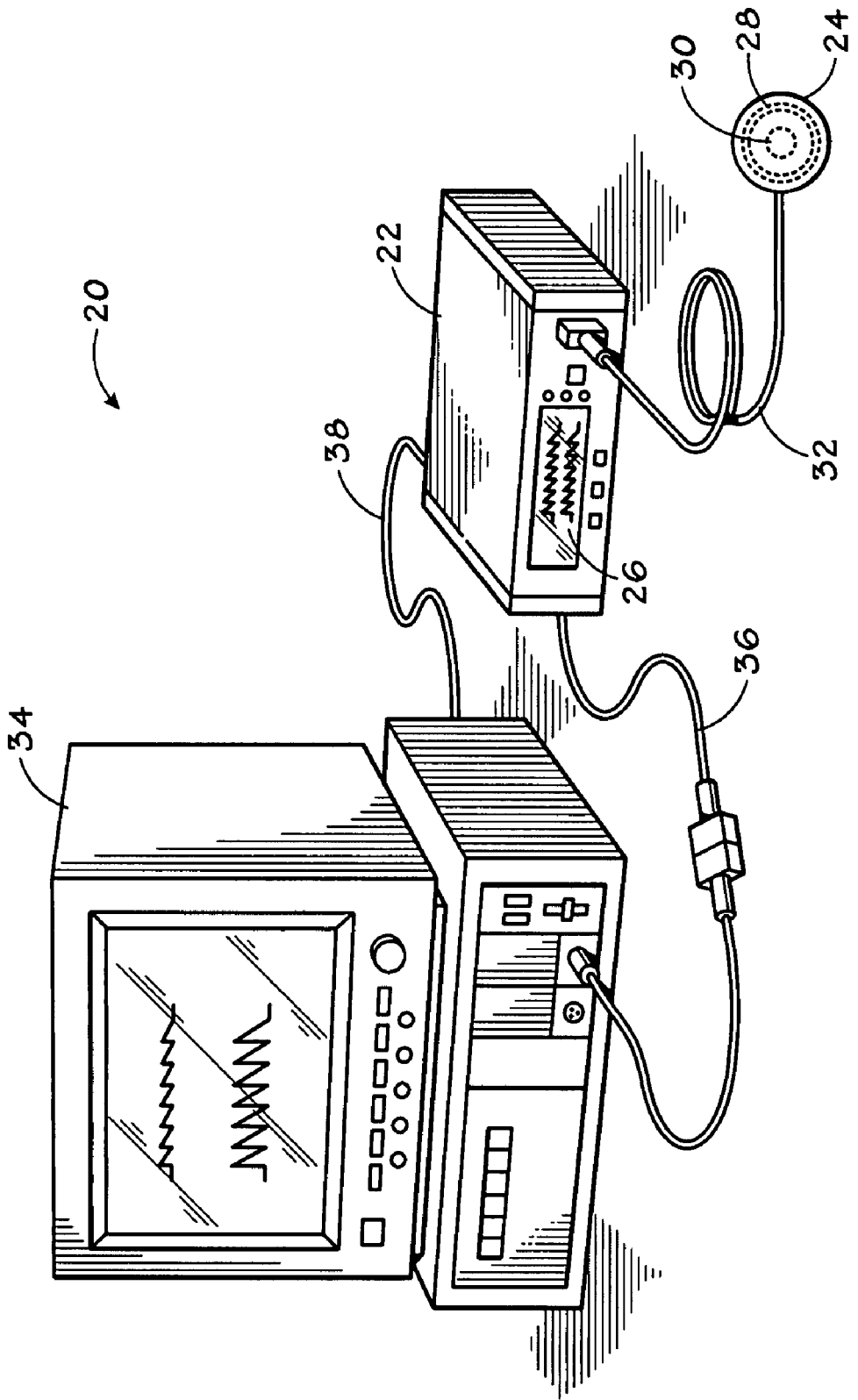
FIG. 2 is a perspective view of a monitor coupled to a multi-parameter patient monitor and a sensor in accordance with an exemplary embodiment of the present invention.

An exemplary system 20 which may be used to determine body fluid metrics, such as HI, in accordance with embodiments of the present invention is shown in FIG. 2. The system 20 may include a monitor 22 and a sensor 24. The monitor 22 may be configured to calculate body fluid metrics and display them on a display 26. The sensor 24 may include an emitter 28 for emitting light into a patient's tissue and a detector 30 for detecting the light after it passes through or is reflected by the patient's tissue. The sensor 24 may be communicatively coupled to the monitor 22 via a cable 32 or other suitable device, such as, for example, a wireless transmission device (not shown).

The system 20 may also include a multi-parameter patient monitor 34. The multi-parameter patient monitor 34 may be included in the system 20 to provide a central display for information from the monitor 22 and from other medical monitoring devices or systems (not shown). For example, the multi-parameter patient monitor 34 may display a patient's body fluid metrics from the monitor 22 along with a blood pressure measurement received from a blood pressure monitor (not shown). In addition to the monitor 22, or alternatively, the multi-parameter patient monitor 34 may be configured to calculate body fluid metrics. The monitor 22 may be communicatively coupled to the multi-parameter patient monitor 34 via a cable 36 or 38 coupled to a sensor input port or a digital communications port, respectively.

Figure 3:
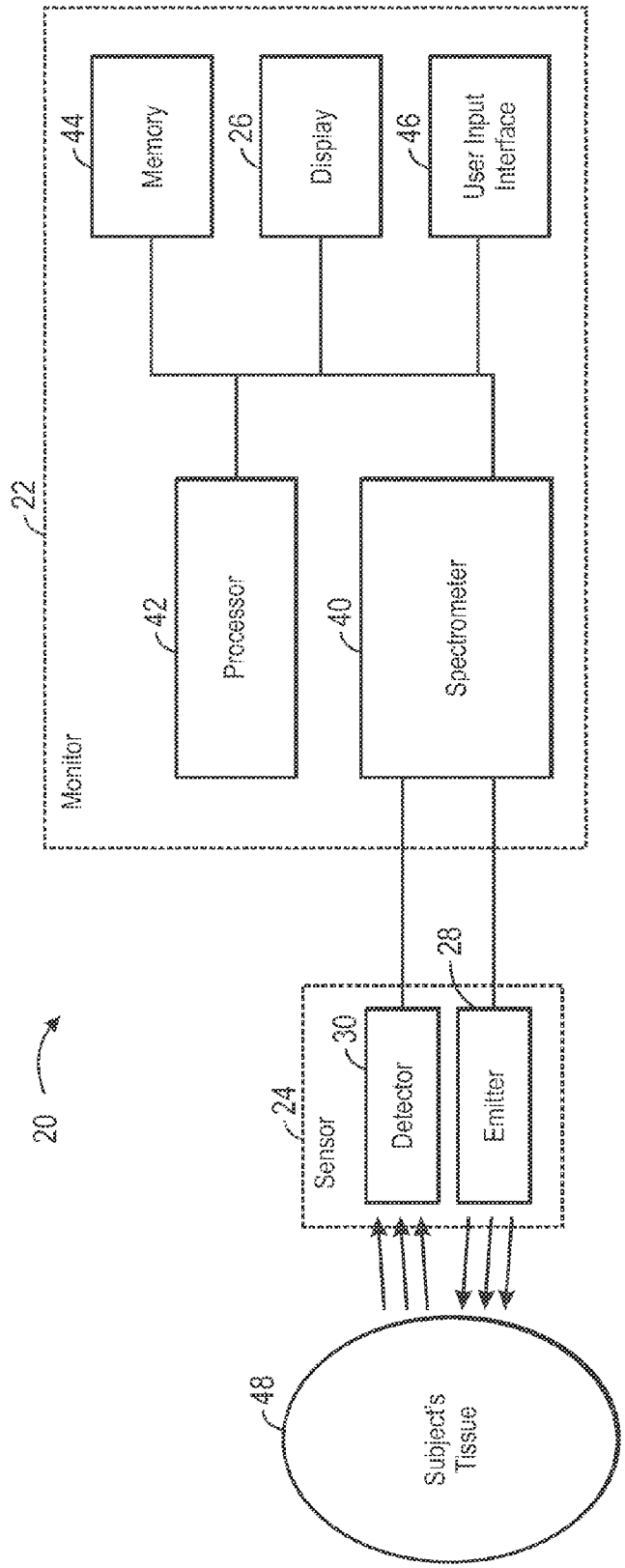
FIG. 3 is a block diagram of the monitor coupled to a patient in accordance with an exemplary embodiment of the present invention.

FIG. 3 is a block diagram of the exemplary system 20 of FIG. 2. Specifically, certain components of the monitor 22 and the sensor 24 are illustrated in FIG. 3. The monitor 22 generally includes a spectrometer 40, a processor 42, a memory 44, the display 26, and an input interface 46. More specifically, the monitor 22 may include components found in oximeters and tissue hydration monitors under development by Nellcor Puritan Bennett LLC of Pleasanton, Calif., such as those disclosed in the references mentioned above.

The sensor 24 includes the emitter 28 and the detector 30. Light emission and detection through the sensor 24 may be controlled by the spectrometer 40. It should be noted that the emitter 28 is configured to emit a range of wavelengths of light into a patient's tissue 48. Hence, the emitter 28 may include a plurality of illumination fibers for emitting light into the patient's tissue 48. The detector 30 may also consist of a plurality of detection fibers and may be configured to transmit light to the spectrometer 40 via the fibers. Light enters the detector 30 after passing through the patient's tissue 48. The spectrometer 40 may convert the intensity of the received light as a function of wavelength into an electrical signal for processing. The light intensity is directly related to the absorbance, scattering, and/or reflectance of light in the tissue 48. That is, when more light at a certain wavelength is absorbed, scattered, or reflected, less light of that wavelength is received from the tissue 48 by the detector 30. In the illustrated embodiment of the sensor 24 in FIG. 2, the illumination fibers making up emitter 28 are arranged in a circle around the detector 30. Other embodiments of the sensor 24 may include, for example, a circular detector surrounding an emitter or a parallel emitter and detector.

The detected light from the detector 30 may be transmitted to the spectrometer 40 in the monitor 22. The spectrometer 40 separates the detected light according to wavelength and converts the intensity to a measure of absorbance to determine an absorbance spectrum. The processor 42 may then perform a multi-linear regression on the measured absorbance spectrum, as described below, using estimated or standardized absorbance spectra of the individual tissue constituents. An algorithm for performing the multi-linear regression, as described below, along with the absorbance spectra information for each of the individual tissue constituents, may be stored in the memory 44. Additional information for use in the multi-linear regression algorithm, such as, for example, the subject's body or skin temperature, may be entered into the monitor 22 via the input interface 46 or via other sensor input ports (not shown).

Figure 4:
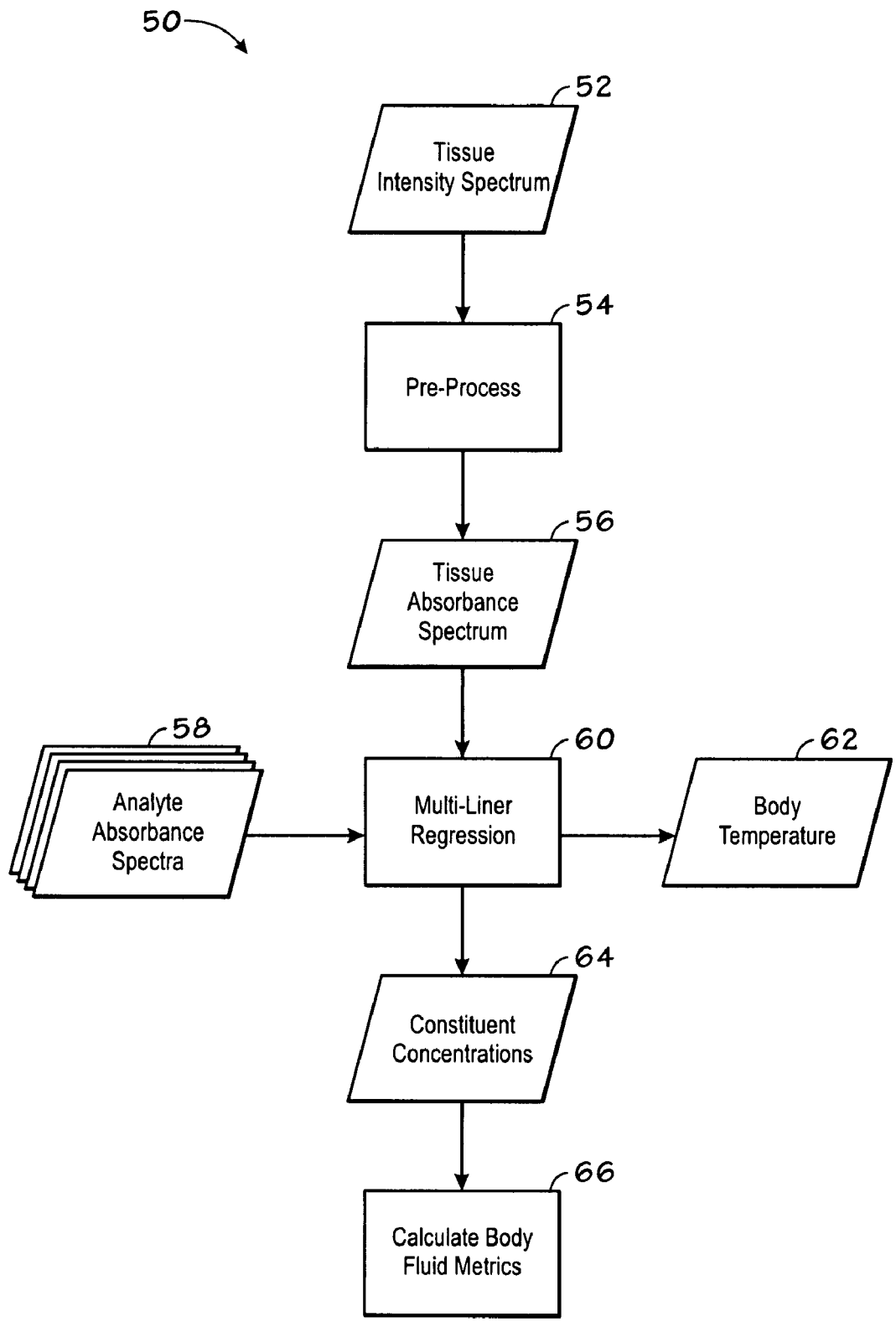
FIG. 4 is a flow chart of a process related to calculating body fluid metrics in accordance with an exemplary embodiment of the present invention.

The monitor 22 may be configured to calculate the hydration index, or other tissue hydration parameters, of a patient's tissue 38 by performing a multi-linear regression of a measured tissue absorbance spectrum in relation to absorbance spectra of known tissue constituents. FIG. 4 is a flow chart illustrating a process 50 by which body fluid metrics may be estimated. The intensity of light detected by detector 30 may be represented as a tissue intensity spectrum 52. The tissue intensity spectrum 52 may be pre-processed (Block 54), as described below, to produce a tissue absorbance spectrum 56. This tissue absorbance spectrum 56 may be compared to a plurality of analyte absorbance spectra 58 in a multi-linear regression (Block 60). In addition, other factors may be considered in the multi-linear regression (Block 60). For example, a patient's body temperature 62 may be input into the multi-linear regression (Block 60) as described below. The result of the multi-linear regression (Block 60) is the constituent concentrations 64. These constituent concentrations 64 may then be used to calculate body fluid metrics (Block 66) as described below.

The data pre-processing step (Block 54) may include correcting the spectrum of detected light 52 for instrument and sensor factors and converting the intensity spectrum 52 into the absorbance spectrum 56. An instrument factor may include, for example, a residual signal detected by the spectrometer 40 with the light source off, due to either ambient light or an offset voltage in the spectrometer's electronic circuitry. This residual signal may be subtracted from the tissue intensity spectrum 52 to correct associated inaccuracies. Another instrument factor may include differences in spectral resolutions between spectrometers, which may cause measurement inaccuracies. For example, the spectrometer 40 may have a different spectral resolution than the spectrometer on which the analyte absorbance spectra 58 were collected. This factor may be corrected by adjusting the known analyte absorbance spectra 58 for the spectral resolution of the spectrometer. That is, the resolution of the analyte absorbance spectra 58 may be scaled up or down depending on the resolutions of the spectrometer on which they were collected and the spectrometer 40 on which the patient's tissue 48 is measured.

Additional instrument and sensor factors may affect the detected intensity spectrum 52. These factors may be corrected in the conversion of the intensity spectrum 52 to the absorbance spectrum 56. Generally, intensity may be converted to absorbance according to the following equation:

$$A = -\log[I_{detected}/I_{emitted}] \quad (1)$$

where I is the intensity of light and A is absorbance. In accordance with present embodiments, $I_{emitted}$ may be adjusted to account for sensor factors which affect the accuracy of Equation (1). For example, the spacing between the emitter 28 and the detector 30 on the sensor 24 may affect the slope and curvature of the detected intensity spectrum 52. Therefore, the detected intensity spectrum 52 may be divided by a reference intensity spectrum of a substance having minimal absorption and scattering similar to tissue. For example, a Teflon block has been found to approximate the bulk scattering of tissue. This Teflon block reference intensity spectrum may further be divided by the ratio of a previously-collected Teflon intensity spectrum to a previously-collected intensity spectrum of a total reflecting substance, such as a gold mirror. While a total reflecting surface may be used directly to establish the reference intensity spectrum, it may be desirable to use the Teflon block with a correction factor to establish the reference intensity spectrum because the Teflon block may be more portable and convenient than, for instance, a gold mirror.

The slope and curvature of the detected tissue intensity spectrum 52 may change with emitter-detector spacing as the scattering coefficients, and therefore the mean photon pathlengths, vary with wavelength. Therefore, the gold-to-Teflon ratio may be calculated and applied for the emitter-detector spacing used to collect the tissue intensity spectrum 52. The corrected reference spectrum compensates for wavelength-dependent emitter and detector characteristics according to the following equations:

$$A = -\log[I_{detected}/I_{standard}], \quad (2)$$

where $$I_{standard} = I_{Teflon,detected} \times \frac{I_{gold,standard}}{I_{Teflon,standard}}.$$

Figure 5:
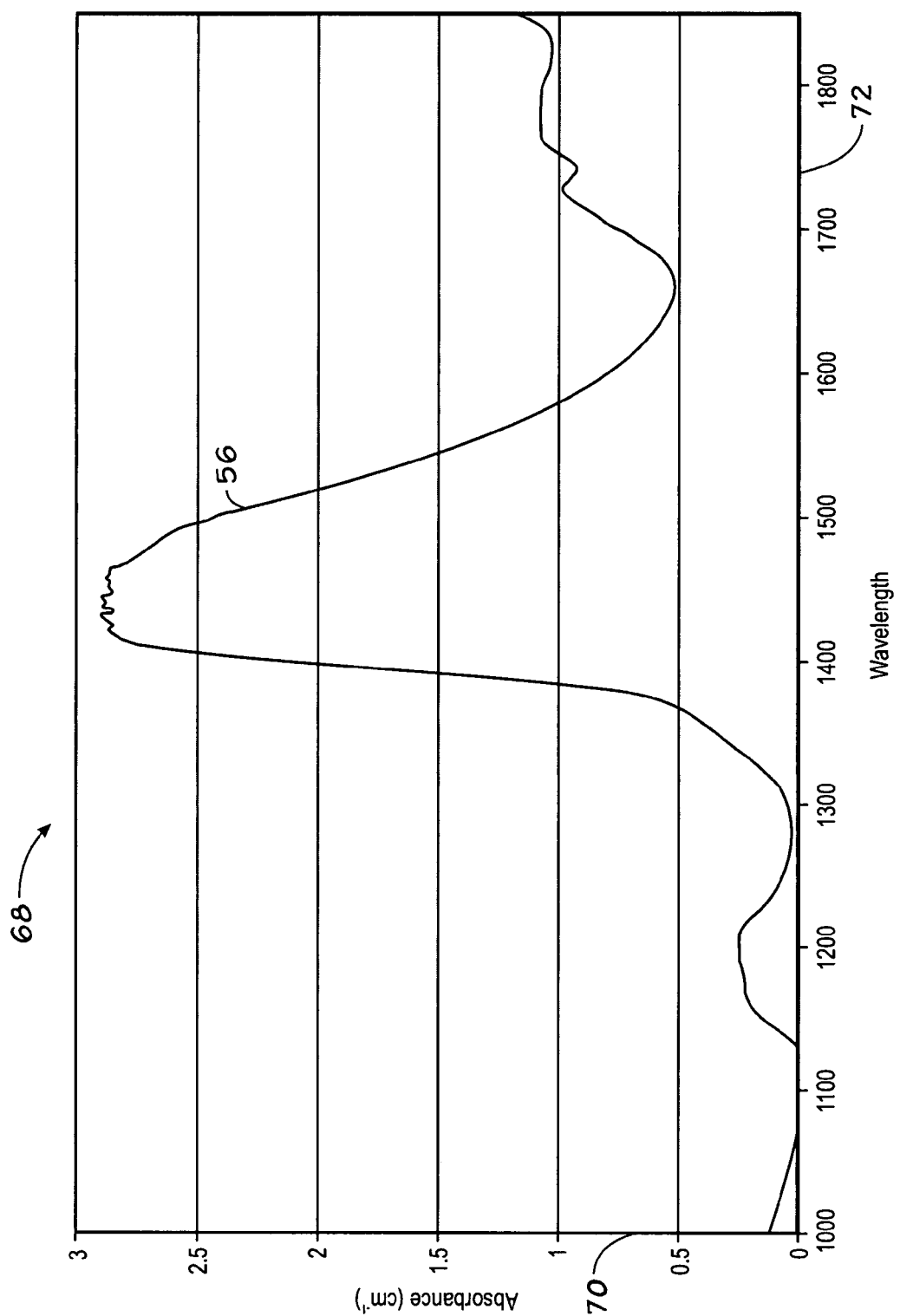
FIG. 5 is a graph of a skin absorbance spectrum as observed in accordance with an exemplary embodiment of the present invention.

Those skilled in the art will recognize that, depending on the design of the monitor 22, $I_{standard}$ may be acquired for each use, may be stored in the memory 44 or in a memory within the sensor 24, or may be computed based on one or more measured or stored instrument or sensor characteristics. The resulting absorbance spectrum 56 represents the absorbance of the patient's tissue 48 across a range of wavelengths, as illustrated by an exemplary graph 68 in FIG. 5. Specifically, the graph 68 includes absorbance values 70 plotted against wavelengths of emitted light 72.

Figure 6:
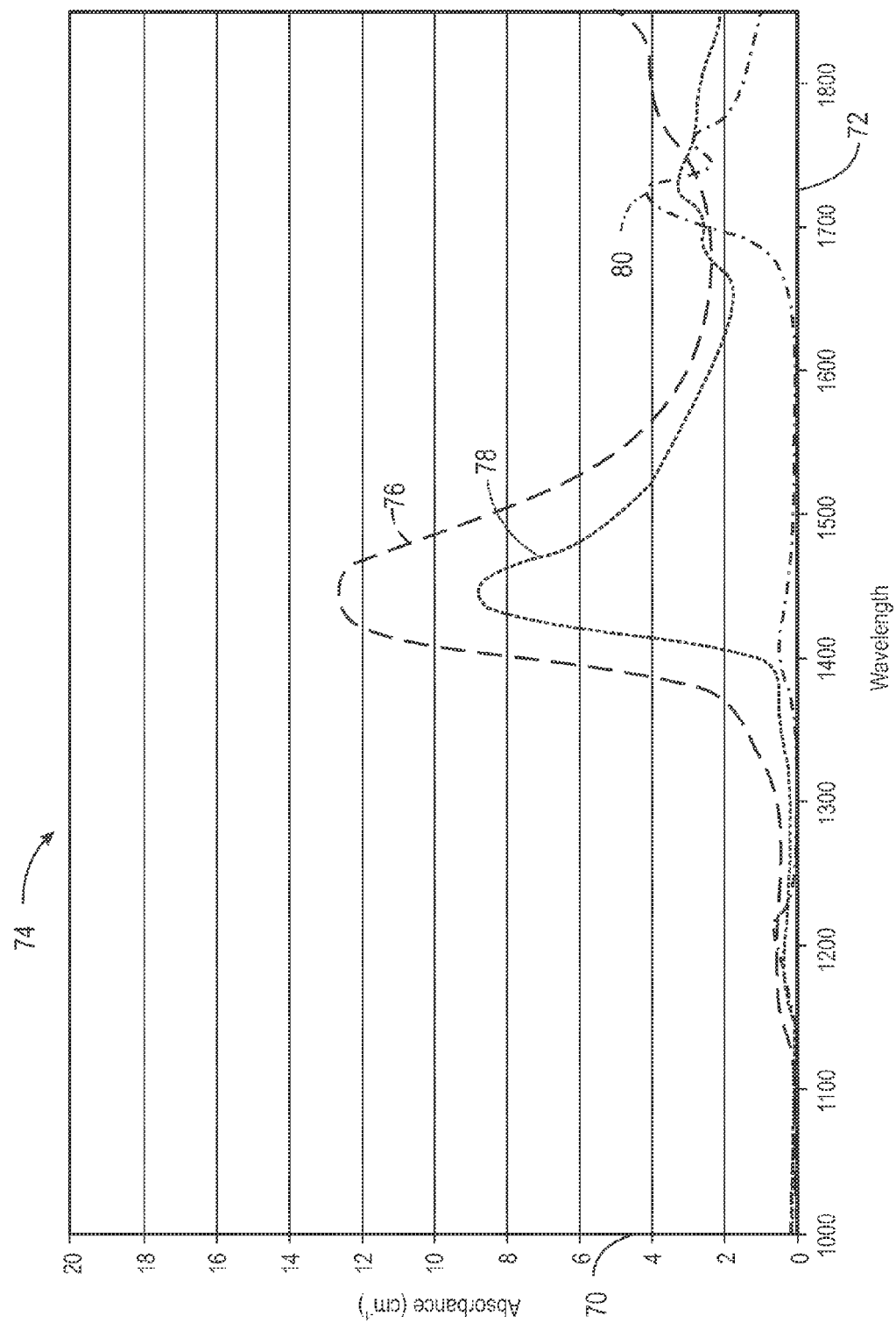
FIG. 6 is a graph of analyte absorbance spectra as observed in accordance with an exemplary embodiment of the present invention.

Returning to FIG. 4, in order to perform the multi-linear regression (Block 60) of the skin tissue absorbance spectrum 56, the absorbance spectra 58 of the main constituents found in skin may be measured or approximated over the entire near-infrared region (i.e., approximately 1000-2500 nm). For example, FIG. 6 includes a graph 74 of the absorbance spectra 58 of known analytes representing some skin constituents. The illustrated absorbance spectra 58 include a water absorbance spectrum 76, a protein absorbance spectrum 78, and a lipid (fat) absorbance spectrum 80. Other analytes for which known absorbance spectra may be collected and which may be used in embodiments of the present invention include oxygenated hemoglobin ($HbO_2$); deoxygenated hemoglobin (Hb); water at different temperatures; known mixtures of water, protein, and lipid; different varieties of proteins (e.g., elastin, albumin, keratin, and collagens); different varieties of lipids (e.g., oleic acid, cholesterol, palmitic acid, corn oil and canola oil); saturated and unsaturated fats; proteins dissolved in deuterium oxide ("heavy water"); and any other analyte representative of known skin constituents. The absorbance spectra 58 may be acquired by measuring light transmitted through a cuvette containing the representative, and desirably non-scattering, analyte.

Referring again to FIG. 4, based on the measured analyte absorbance spectra 58, the concentration of skin constituents 64 may be determined from the tissue absorbance spectrum 56 in the multi-linear regression (Block 60). Multi-linear regression may be employed to determine a linear combination of the known analyte absorbance spectra 58, such as absorbance spectra 76, 78, and 80, that best matches the measured tissue absorbance spectrum 56. In other words, the multi-linear regression determines to what extent each tissue constituent contributes to the values of the measured tissue absorbance spectrum 56. The multi-linear regression (Block 60) may be characterized by the following set of equations:

$$A_{\lambda_1}^M = C_W A_{\lambda_1}^W + C_P A_{\lambda_1}^P + C_L A_{\lambda_1}^L + C_H A_{\lambda_1}^H + b$$

$$A_{\lambda_2}^M = C_W A_{\lambda_2}^W + C_P A_{\lambda_2}^P + C_L A_{\lambda_2}^L + C_H A_{\lambda_2}^H + b$$

$$A_{\lambda_n}^M = C_W A_{\lambda_n}^W + C_P A_{\lambda_n}^P + C_L A_{\lambda_n}^L + C_H A_{\lambda_n}^H + b \quad (3)$$

where A is the absorbance, $\lambda_n$ is the wavelength, C is the concentration 64 of the constituent, b is a wavelength-independent offset, M denotes the measured tissue 48, W denotes water, P denotes proteins, L denotes lipids, and H denotes oxygenated hemoglobin. Additional terms may be added for other analytes. This system may also be expressed using the following equation:

$$A^M = A^S C, \quad (4)$$

$$\text{where } A^M = \begin{pmatrix} A_{\lambda_1}^T \\ A_{\lambda_2}^T \\ \vdots \\ A_{\lambda_N}^T \end{pmatrix}, C = \begin{pmatrix} C_W \\ C_P \\ C_L \\ C_H \\ b \end{pmatrix}, \text{ and}$$

$$A^S = \begin{pmatrix} A_{\lambda_1}^W & A_{\lambda_1}^P & A_{\lambda_1}^L & A_{\lambda_1}^H & 1 \\ A_{\lambda_2}^W & A_{\lambda_2}^P & A_{\lambda_2}^L & A_{\lambda_2}^H & 1 \\ \vdots & \vdots & \vdots & \vdots & \vdots \\ A_{\lambda_N}^W & A_{\lambda_N}^P & A_{\lambda_N}^L & A_{\lambda_N}^H & 1 \end{pmatrix}.$$

Given the measured tissue absorbance spectrum 56 ($A^M$) and the known analyte absorbance spectra 58 ($A^S$), the concentration 64 (C) of each constituent may be calculated. Because the measured tissue absorbance spectrum 56 and the known analyte absorbance spectra 58 may be represented as matrices, as illustrated in Equation (4), solving for the constituent concentrations 64 may be performed using a suitable matrix manipulation environment, such as, for example, MATLAB®, available commercially from The MathWorks, Natick, Mass. The matrix manipulation environment may, for example, be utilized to find the constituent concentrations 64 (C) in Equation (4) by multiplying each side of the equation by the inverse of the matrix representing the analyte absorbance spectra 58 ($A^S$). The matrix manipulation environment may, for example, be stored in the memory 44 of the monitor 22 for use by the processor 42.

Equations (3) and (4) illustrate a simple multi-linear regression model which considers only four skin constituents and a wavelength-independent offset which accounts for variations in light input. Additional factors may be added to the equations to account for observed differences in estimated and actual body fluid metrics. For example, the multi-linear regression model may include a temperature component to account for temperature-dependent changes in hydrogen bonding which affect the width and center frequency of the water absorbance spectrum 76. That is, the patient's body or skin temperature 62 may be measured and used as an input to the model. The effect of temperature on the water absorbance spectrum 76 is due to hydrogen bonds between molecules which decrease as temperature increases. In addition, it is believed that the degree of hydrogen bonding could be affected in vivo by the proximity of water molecules to either fat or protein and/or by the structural properties of the tissue rather than the bulk composition. The temperature component of the multi-linear regression model may include adjustment of the known water absorbance spectrum 76 for the measured body temperature 62 and/or use of a specific known water absorbance spectrum 76 corresponding to the measured temperature 62. Thus, equation (3) may be rewritten as follows:

$$A_{\lambda_n}^M = C_W A_{\lambda_n}^W(T) + C_P A_{\lambda_n}^P + C_L A_{\lambda_n}^L + C_H A_{\lambda_n}^H + b \quad (5)$$

where T is the patient's body temperature 62, and the known absorbance spectrum of water 76 ($A^W$) is dependent on temperature 62.

Further adjustments to the multi-linear regression model may consist of, for example, adding a slope factor in addition to the known analyte absorbance spectra ($A^S$) and the wavelength-independent offset (b). This slope factor may account for variation between tissues in the derivative of the tissue scattering coefficient with respect to wavelength which are independent of variation in the composition of the tissue. The slope factor may consist of, for example, another degree of freedom in the multi-linear regression and/or a known offset. Equation (5) may therefore be rewritten as follows:

$$A_{\lambda_n}^M = C_W A_{\lambda_n}^W(T) + C_P A_{\lambda_n}^P + C_L A_{\lambda_n}^L + C_H A_{\lambda_n}^H + b + s_{\lambda_n} \quad (6)$$

where s represents the slope factor. The slope factor may, for example, be a linear function, a quadratic or higher order polynomial function, or an exponential function of wavelength.

An additional factor may be added to the multi-linear regression model to account for the reduction in mean photon pathlength that occurs with increasing absorption coefficients. That is, tissue that is more absorbent at a given wavelength will preferentially absorb light deeper in the tissue, so that the photons reaching the detector will preferentially be those that traversed a shallower and shorter path through the tissue. This pathlength factor may be represented as a weighted function of the measured tissue absorbance spectrum. For example, the function may be a multiple of the square of the tissue absorbance spectrum 56 (($A^M)^2$). In addition, if a spectrometer is used in which the wavelength calibration drifts, a weighted derivative of the tissue absorbance spectrum with respect to wavelength ($dA^M/d\lambda$) may be added as a calibration factor to the multi-linear regression model to account for shifts in the wavelength calibration. Including these pathlength and calibration factors, Equation (6) may be rewritten as follows:

$$A_{\lambda_n}^M = C_W A_{\lambda_n}^W(T) + C_P A_{\lambda_n}^P + \qquad (7)$$
$$C_L A_{\lambda_n}^L + C_H A_{\lambda_n}^H + b + s_{\lambda_n} + \alpha(A_{\lambda_n}^M)^2 + \beta \frac{dA_{\lambda_n}^M}{d\lambda},$$

where α and β are weighting coefficients.

A correction may also be made to account for the water content of fat (approximately 10-20%) and to exclude this fat-associated water from the lean-water estimate. Finally, hydration index, approximated as the ratio of water to non-fat analytes, may be computed (Block 66) based on the concentrations of each tissue constituent obtained from the multi-linear regression according to the following equation:

$$HI = \frac{C_W}{C_W + C_P + C_H}. \qquad (8)$$

Figure 7:
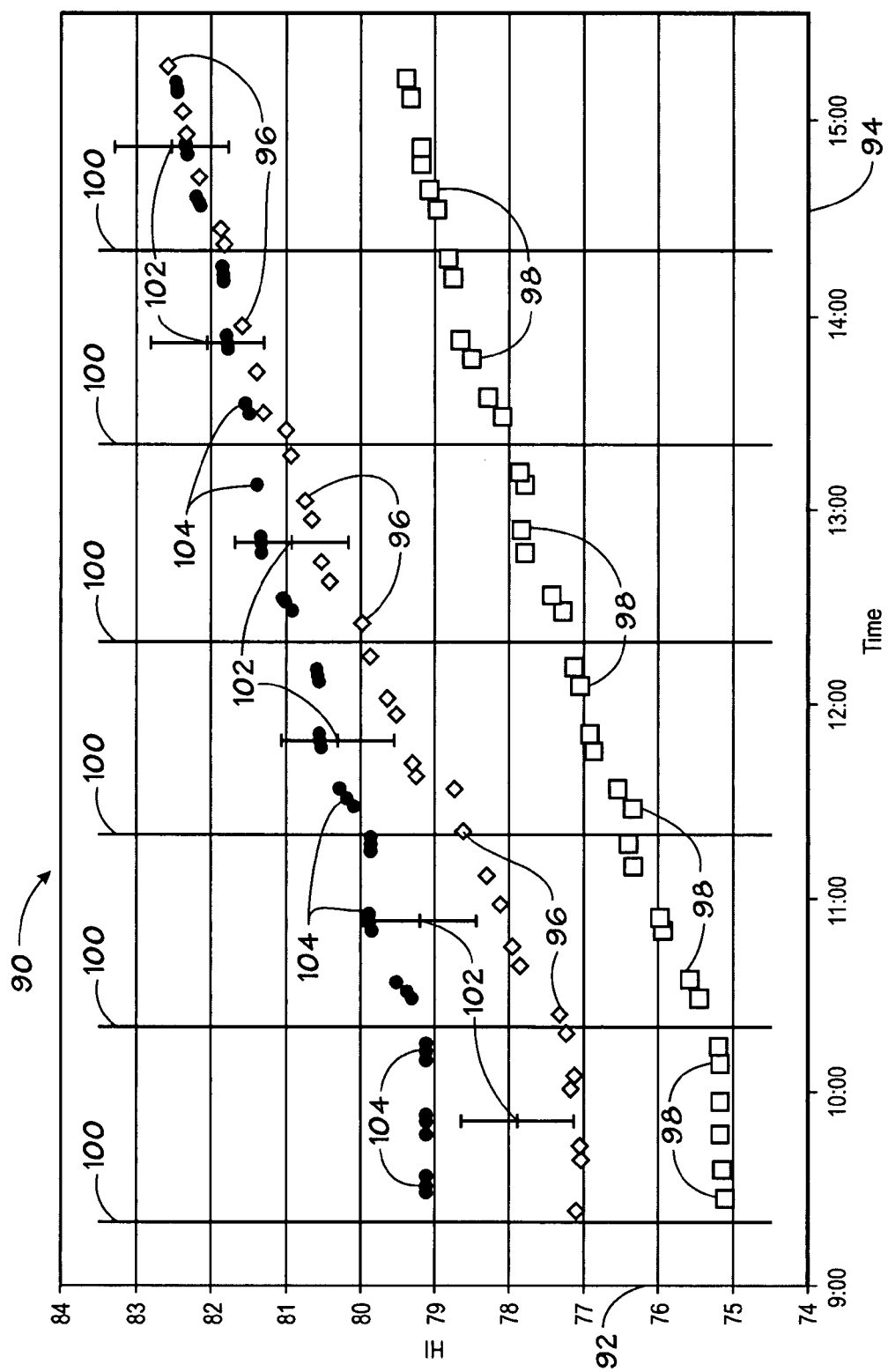
FIG. 7 is a graph of a pig's hydration index as measured while the pig underwent overhydration in accordance with an exemplary embodiment of the present invention.

In an experimental test of the described multi-linear regression model, the algorithm was applied to data collected from both euhydrated humans and overhydrated pigs. These tissue absorbance spectra were gathered from a near-infrared array spectrometer with spectral resolution of about 18 nm. FIG. 7 includes a graph 90 that illustrates the results of an exemplary test of a pig undergoing overhydration. The graph 90 shows HI 92 over time 94 according to embodiments of the present invention. The measured tissue absorbance spectra used in calculating HI were obtained using a torso sensor (data points 96) and a forehead sensor (data points 98). The emitter-detector spacing for the torso sensor was 5 mm and for the forehead sensor was 9 mm, and the wavelength range analyzed was 1000-1350 nm. Each vertical line 100 marks the time at which half a liter of fluid was administered to the subject.

In addition to estimating the HI, data collected by local biopsy (data points 102) was analyzed by chemical methods, such as those described in S. E. Campbell et al., "A novel method to determine lean body water using localized skin biopsies: correlation between lean skin water and lean body water in an overhydration model," *American Journal of Physiology—Regulatory, Integrative and Comparative Physiology* 291 (2006), R1539-R1544, which is herein incorporated by reference in its entirety for all purposes. Whole body water fraction was calculated using the same chemical analysis method on the homogenized carcass after the end of the experiment. Weights measured during the course of each measurement were then used to back-calculate body water fractions (data points 104). It is apparent from the graph 90 that the multi-linear regression method for estimating HI shows high correlation to chemical analyses of local skin biopsies and back-calculation of body water fractions from the homogenized carcass. Indeed, the data points obtained from each method clearly include similar trends.

Figure 8:
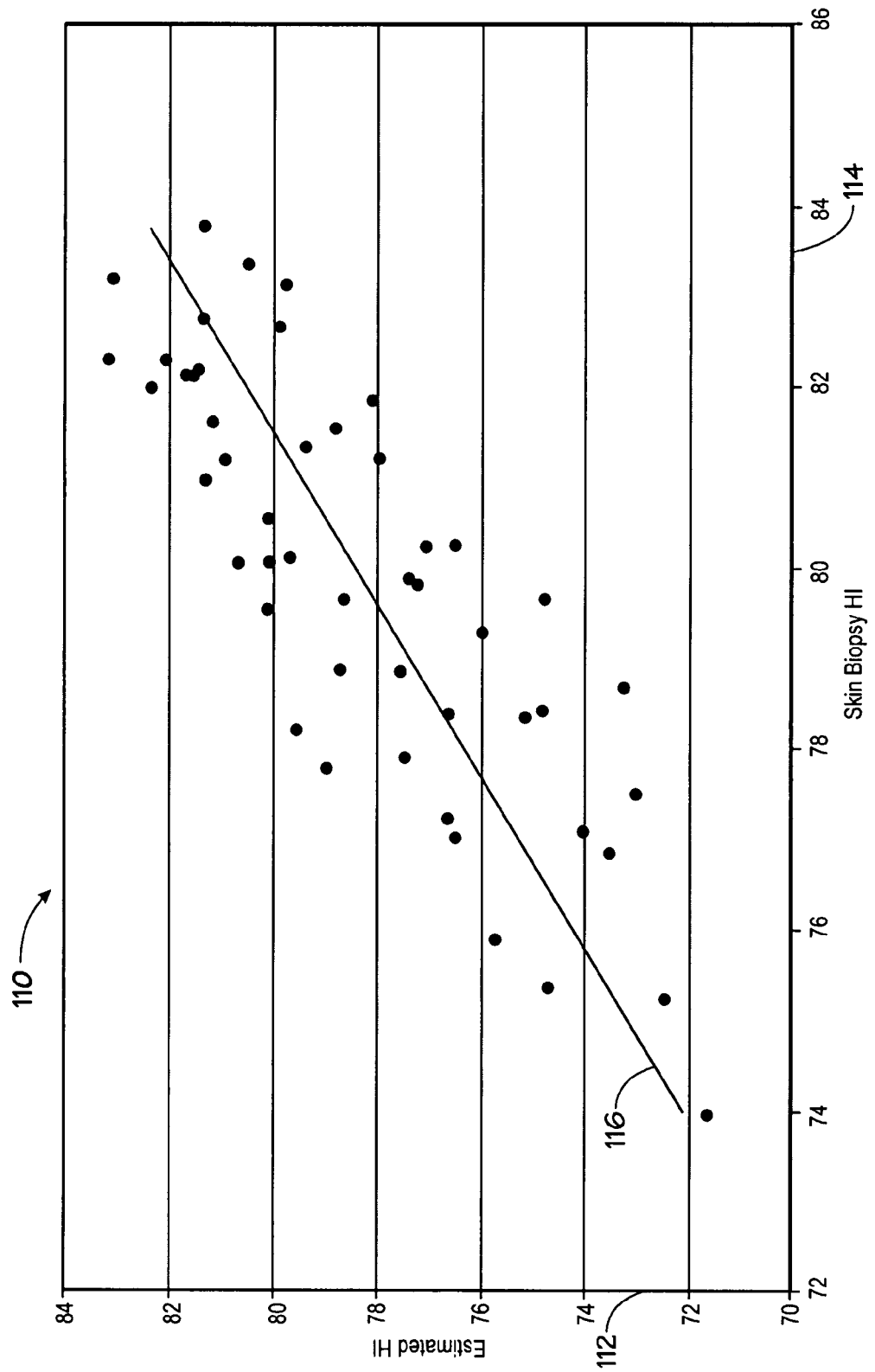
FIG. 8 is a graph of hydration index as determined by a monitor versus hydration index as determined by local skin biopsy for a study of eight pigs undergoing overhydration as observed in accordance with an exemplary embodiment of the present invention.

Results of further experimentation on eight overhydrated pigs, illustrated in a graph 110 included in FIG. 8, show a good correlation between estimated HI 112 from the multi-linear regression model and HI 114 determined by skin biopsy. A torso sensor with an emitter-detector spacing of 2.5 mm and a wavelength range of 1000-1350 nm was used to collect data for the multi-linear regression. A linear trendline 116 describing the relationship between the estimated HI 112 and the skin biopsy HI 114 has an R-squared value of 0.68. An R-squared value of one would represent a perfect correlation between the estimated HI 112 and the skin biopsy HI 114.

Figure 9:
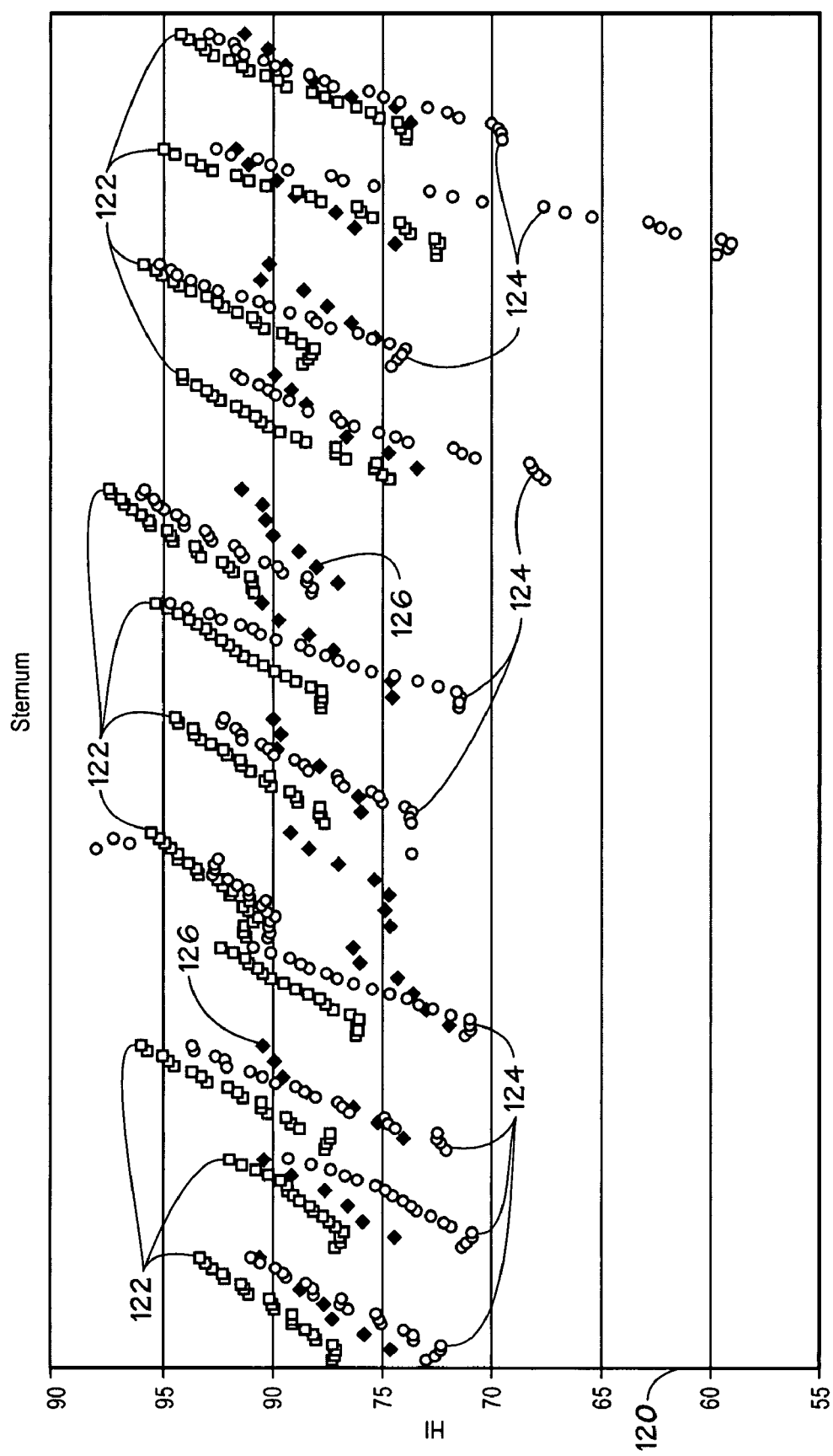
FIGS. 9-13 are graphs illustrating a correlation between hydration index as determined by local skin biopsy and estimated hydration index calculated at various sensor sites using each of two wavelength bands for a study of twelve pigs undergoing non-isotonic overhydration as observed in accordance with an exemplary embodiment of the present invention.
Figure 10:
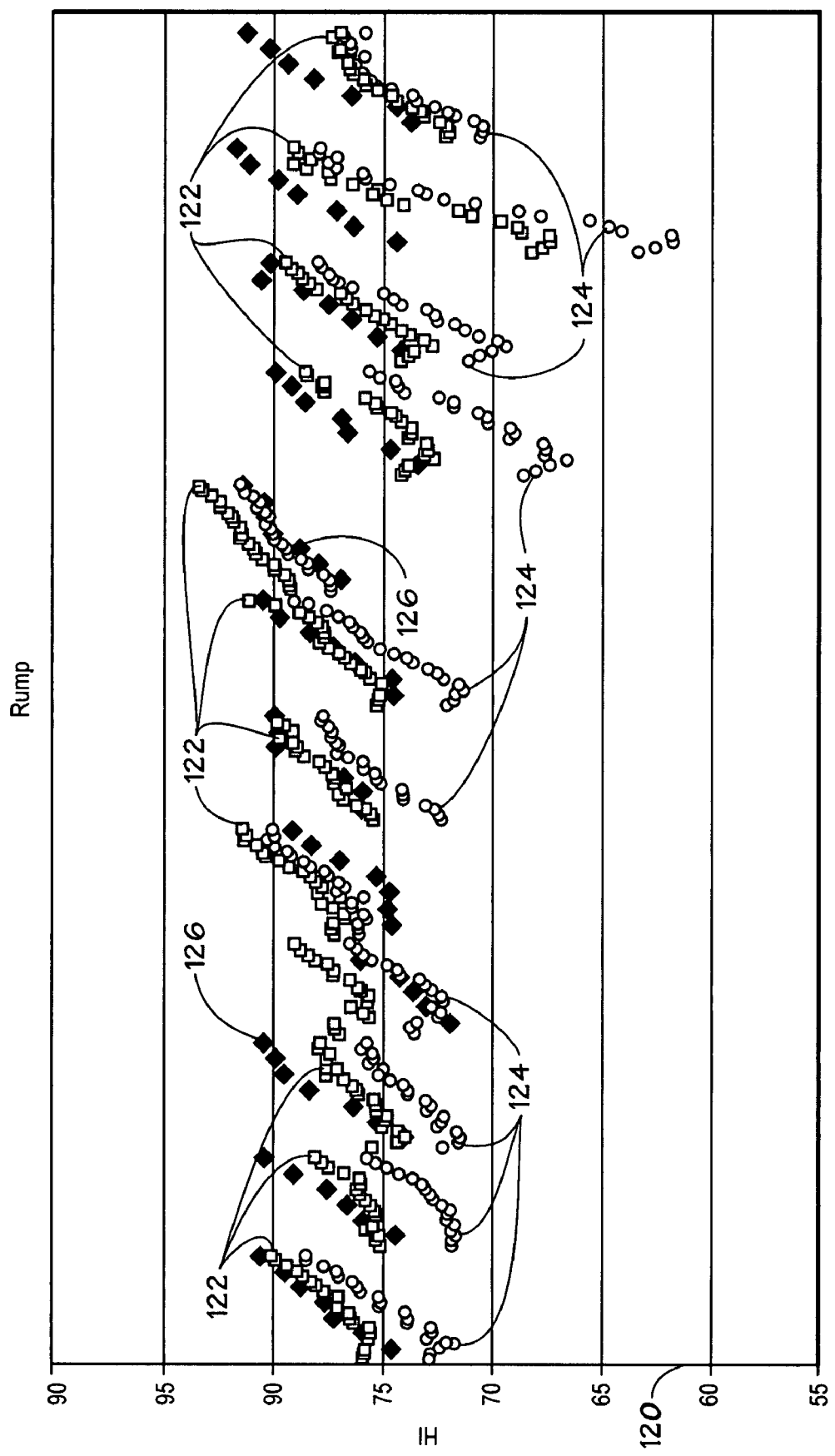
Figure 11:
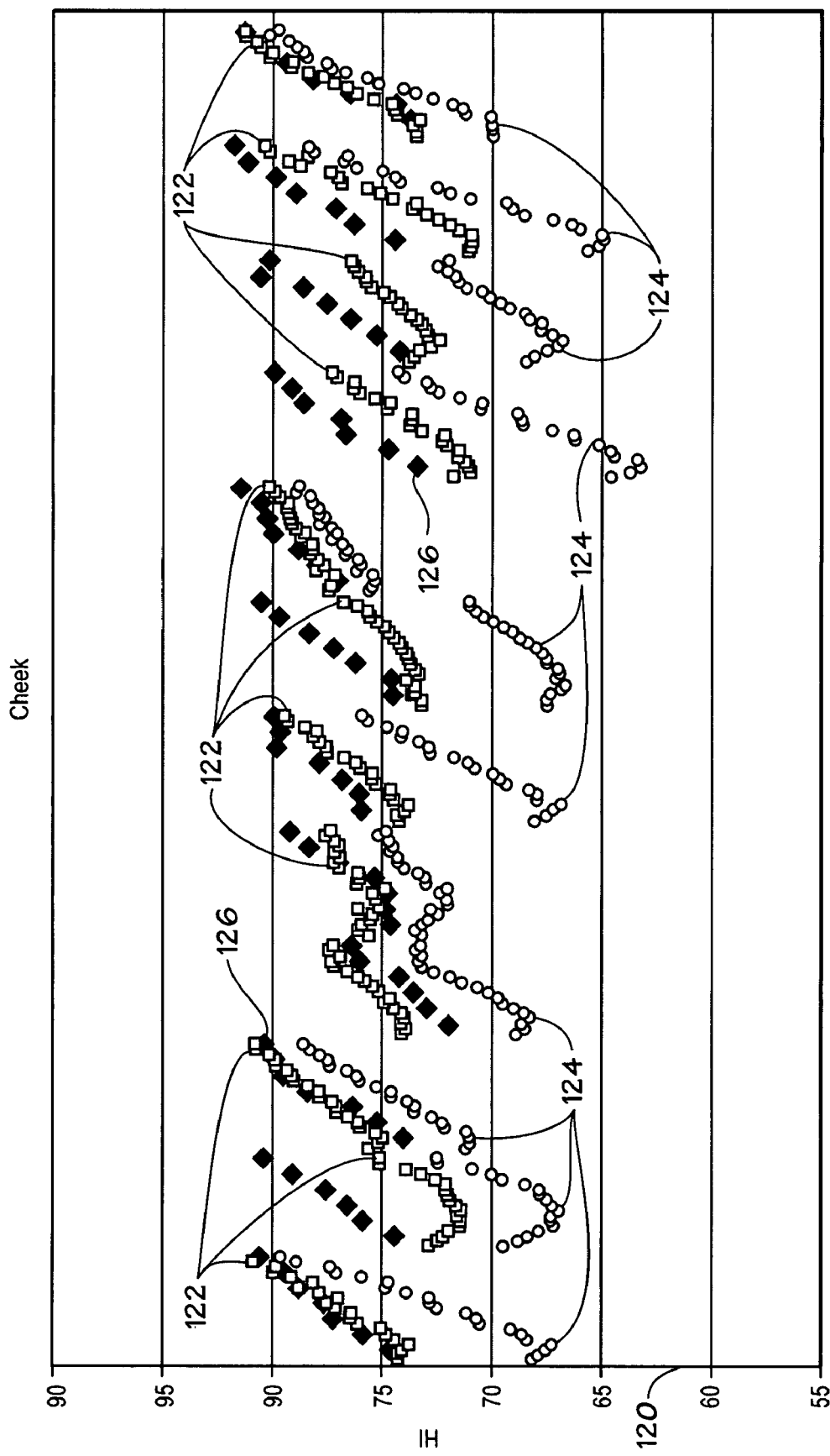
Figure 12:
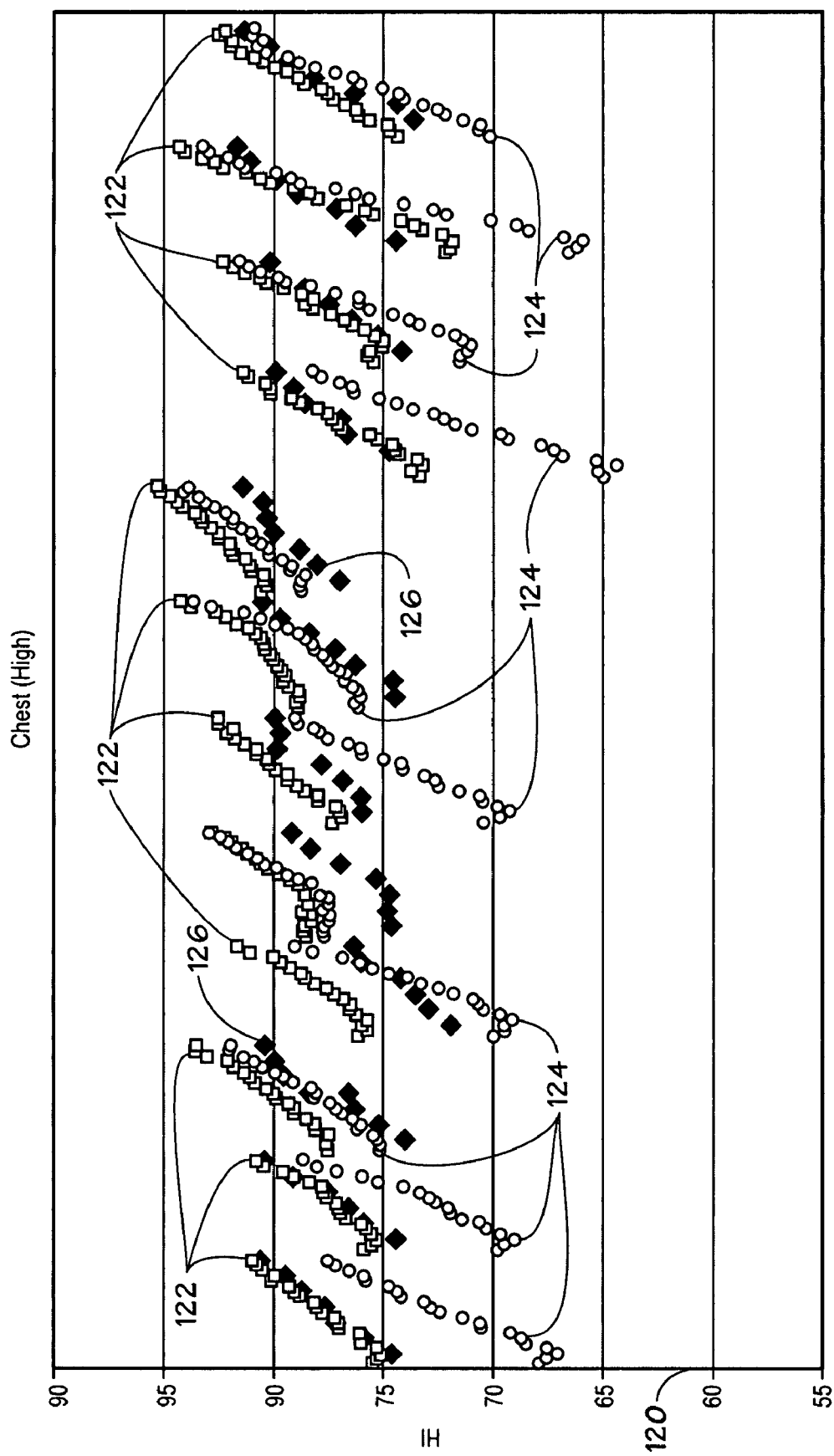
Figure 13:
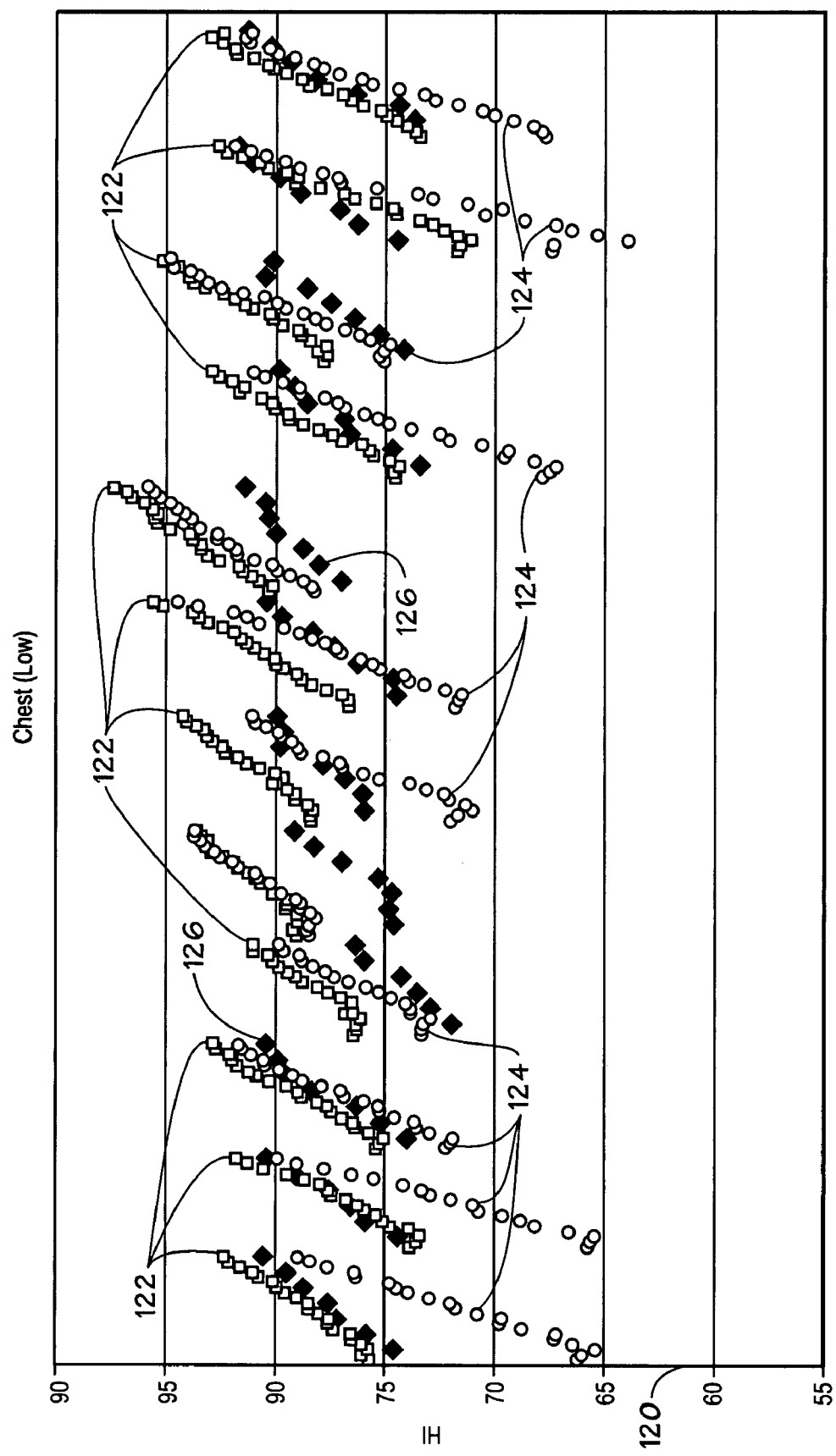

In addition, FIGS. 9-13 illustrate the results of a non-isotonic overhydration study performed on twelve pigs in which a hydration index 120 was calculated from sensors placed at five different locations on the pigs' bodies. In FIG. 9, the sensors were placed on the pigs' sterna; in FIG. 10, the sensors were placed on the rumps; in FIG. 11, the sensors were placed on the cheeks; in FIG. 12, the sensors were placed high on the pigs' chests; and in FIG. 13, the sensors were placed low on the pigs' chests. Data points 122 were calculated from light emitted in the range of 1000-1350 nm, while data points 124 were calculated using light in the range of 1530-1850 nm. One skilled in the art will understand that estimated HI calculated from the 1530-1850 nm range may be lower than the 1000-1350 nm range because the longer wavelengths do not penetrate as deeply into the skin, and shallower skin layers may have lower water content. Data points 126 represent the pigs' hydration indices as determined by skin biopsy. It can be seen from the graphs in FIGS. 9-13 that, for both the 1000-1350 nm range and the 1530-1850 range, the estimated HI (data points 122 and 124) has a high correlation to the chemical analyses from local skin biopsies (data points 126) for the sensor sites tested.

Results from studies such as those illustrated in FIGS. 7-13 show that estimation of HI according to embodiments of the present technique may be useful to apply in a clinical setting. The multi-linear regression method may allow for quick, accurate, and non-invasive determination of HI.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, methemoglobin, total hemoglobin, intravascular dyes, and/or water content. The invention is to cover all modifications, equivalents, and alternatives falling within the spirit and scope of the invention as defined by the following appended claims.

What is claimed is:

1. A method for calculating one or more body fluid metrics, comprising:
   acquiring an absorbance spectrum of a subject's tissue at a range of wavelengths of light;
   determining concentrations of a plurality of constituents of the subject's tissue by performing a multi-linear regression of the absorbance spectrum in relation to a plurality of absorbance spectra of the constituents; and
   calculating one or more body fluid metrics based on the concentrations.

2. The method of claim 1, wherein the one or more body fluid metrics comprises a hydration index.

3. The method of claim 1, wherein the one or more body fluid metrics comprises a percentage of a constituent of the subject's tissue relative to one or more other constituents.

4. The method of claim 1, wherein the range of wavelengths of light comprises a range of wavelengths of near-infrared light.

5. The method of claim 1, wherein the range of wavelengths of light comprises about 1000 nm to about 1350 nm.

6. The method of claim 1, wherein the range of wavelengths of light comprises about 1530 nm to about 1850 nm.

7. The method of claim 1, wherein the plurality of constituents of the subject's tissue comprise water, proteins, lipids, oxygenated hemoglobin, deoxygenated hemoglobin, or a combination thereof.

8. The method of claim 1, comprising acquiring the plurality of absorbance spectra of the constituents.

9. The method of claim 8, wherein acquiring the absorbance spectrum of the constituent comprises:
transmitting the range of wavelengths of light through an analyte representing the constituent;
measuring intensities of the transmitted light for the range of wavelengths; and
converting the intensities to absorbance measurements for the range of wavelengths.

10. The method of claim 1, comprising processing the absorbance spectrum of the subject's tissue, the absorbance spectra of the constituents, or a combination thereof to correct for instrument errors, sensor errors, or a combination thereof.

11. The method of claim 1, wherein performing the multi-linear regression comprises adjusting a constituent absorbance spectrum based on a subject's body temperature.

12. The method of claim 1, wherein performing the multi-linear regression comprises adding a slope factor to account for a tissue scattering coefficient.

13. The method of claim 1, wherein performing the multi-linear regression comprises adding a pathlength factor to account for a change in mean photon pathlength that occurs with a change in absorption coefficients.

14. The method of claim 1, wherein performing the multi-linear regression comprises adding a calibration factor to account for a shift in an instrument calibration.

15. The method of claim 1, wherein acquiring the absorbance spectrum of the subject's tissue comprises:
acquiring an intensity spectrum of the subject's tissue;
adjusting the intensity spectrum of the subject's tissue by comparison to a reference intensity spectrum; and
converting the adjusted intensity spectrum to the absorbance spectrum.

16. The method of claim 15, wherein the reference intensity spectrum comprises an intensity spectrum of a substance having minimal absorption and scattering similar to tissue, a total reflecting substance, or a combination thereof.

17. The method of claim 1, wherein the absorbance spectrum is a wide-band absorbance spectrum.

18. The method of claim 1, wherein performing the multi-linear regression comprises determining a linear combination of the plurality of absorbance spectra of the constituents that best matches the absorbance spectrum.

19. A method for calculating one or more body fluid metrics, comprising: measuring an intensity spectrum of a subject's tissue; processing the intensity spectrum to determine an absorbance spectrum of the tissue; performing a multi-linear regression of the absorbance spectrum in relation to a plurality of analyte absorbance spectra, wherein the analytes are representative of tissue constituents; determining concentrations of the tissue constituents based on the multi-linear regression; and calculating one or more body fluid metrics based on the concentrations.

20. The method of claim 19, comprising determining a relative percentage of at least one tissue constituent to the other tissue constituents.

21. The method of claim 19, wherein the tissue constituents comprise water, proteins, lipids, oxygenated hemoglobin, deoxygenated hemoglobin, or a combination thereof.

22. The method of claim 19, wherein the intensity spectrum of the subject's tissue is measured over a range of near-infrared wavelengths of light.

23. The method of claim 19, wherein the intensity spectrum of the subject's tissue is measured over a range of light from approximately 1000-1350 nm.

24. The method of claim 19, wherein the intensity spectrum of the subject's tissue is measured over a range of light from approximately 1530-1850 nm.

25. The method of claim 19, wherein processing the intensity spectrum comprises adjusting the intensity spectrum to account for a residual instrument signal, a difference in scattering between the intensity spectrum of the subject's tissue and a reference intensity spectrum, or a combination thereof.

26. The method of claim 25, wherein the reference intensity spectrum comprises an intensity spectrum of a substance having minimal absorption and scattering similar to tissue, a total reflecting substance, or a combination thereof.

27. The method of claim 19, wherein performing a multi-linear regression comprises adjusting a constituent absorbance spectrum based on a subject's body temperature, adding a slope factor to account for a tissue scattering coefficient, adding a pathlength factor to account for a change in mean photon pathlength that occurs with a change in absorption coefficients, adding a calibration factor to account for a shift in an instrument calibration, or a combination thereof.

28. The method of claim 19, wherein the absorbance spectrum is a wide-band absorbance spectrum.

29. The method of claim 19, wherein performing the multi-linear regression comprises determining a linear combination of the plurality of analyte absorbance spectra that best matches the absorbance spectrum.

30. A system for calculating one or more body fluid metrics, comprising:
a sensor configured to emit a range of wavelengths of light into a subject's tissue and to detect reflected, scattered, or transmitted light;
a spectrometer configured to process the reflected, scattered, or transmitted light and to generate an absorbance spectrum of the subject's tissue across the range of wavelengths of light;
a memory configured to store a plurality of absorbance spectra of tissue constituents across the range of wavelengths of light and to store a multi-linear regression model; and
a processor configured to perform a multi-linear regression of the absorbance spectrum of the subject's tissue with respect to the plurality of absorbance spectra of tissue constituents based on the multi-linear regression model and to calculate one or more body fluid metrics based on the multi-linear regression.

31. The system of claim 30, wherein the one or more body fluid metrics comprise a hydration index.

32. The system of claim 30, wherein the one or more body fluid metrics comprise a relative percentage of at least one tissue constituent to one or more other tissue constituents.

33. The system of claim 30, comprising a display configured to display the one or more body fluid metrics.

34. The system of claim 30, wherein the multi-linear regression comprises a constituent absorbance spectrum based on a subject's body temperature, a slope factor to account for a tissue scattering coefficient, a pathlength factor to account for a change in mean photon pathlength that occurs with a change in absorption coefficients, a calibration factor to account for a shift in an instrument calibration, or a combination thereof.

35. The system of claim 30, wherein the light emitted by the sensor is a wide-band light.

36. The system of claim 30, wherein the absorbance spectrum is a wide-band absorbance spectrum.

37. The system of claim 30, wherein the multi-linear regression comprises determining a linear combination of the plurality of absorbance spectra of the tissue constituents that best matches the absorbance spectrum.

38. One or more tangible, non-transitory machine-readable media, comprising code executable to perform the acts of:
performing a multi-linear regression of an absorbance spectrum of a subject's tissue in relation to a plurality of absorbance spectra of skin constituents; and
calculating one or more body fluid metrics based on the multi-linear regression.

39. The tangible, non-transitory machine-readable media of claim 38, wherein calculating one or more body fluid metrics comprises calculating a hydration index.

40. The tangible, non-transitory machine-readable media of claim 38, wherein calculating one or more body fluid metrics comprises calculating a percentage of at least one skin constituent relative to one or more other skin constituents.

41. The tangible, non-transitory machine-readable media of claim 38, wherein performing a multi-linear regression comprises adjusting a constituent absorbance spectrum based on a subject's body temperature, adding a slope factor to account for a tissue scattering coefficient, adding a pathlength factor to account for a change in mean photon pathlength that occurs with a change in absorption coefficients, adding a calibration factor to account for a shift in an instrument calibration, or a combination thereof.

42. The tangible, non-transitory machine-readable media of claim 38, wherein the absorbance spectrum is a wide-band absorbance spectrum.

43. The tangible, non-transitory machine-readable media of claim 38, wherein performing the multi-linear regression comprises determining a linear combination of the plurality of absorbance spectra of the skin constituents that best matches the absorbance spectrum.

44. A monitor for calculating one or more body fluid metrics, comprising:

a spectrometer configured to process light acquired from detection of reflected, scattered, or transmitted light emitted at a range of wavelengths into a subject's tissue and to generate an absorbance spectrum of the subject's tissue across the range of wavelengths of light;
a memory configured to store a plurality of absorbance spectra of tissue constituents across the range of wavelengths of light and to store a multi-linear regression model; and
a processor configured to perform a multi-linear regression of the absorbance spectrum of the subject's tissue with respect to the plurality of absorbance spectra of tissue constituents based on the multi-linear regression model and to calculate one or more body fluid metrics based on the multi-linear regression.

45. The monitor of claim 44, wherein the one or more body fluid metrics comprise a hydration index.

46. The monitor of claim 44, wherein the one or more body fluid metrics comprise a relative percentage of at least one tissue constituent to one or more other tissue constituents.

47. The monitor of claim 44, comprising a display configured to display the one or more body fluid metrics.

48. The monitor of claim 44, wherein the multi-linear regression comprises a constituent absorbance spectrum based on a subject's body temperature, a slope factor to account for a tissue scattering coefficient, a pathlength factor to account for a change in mean photon pathlength that occurs with a change in absorption coefficients, a calibration factor to account for a shift in an instrument calibration, or a combination thereof.

49. The monitor of claim 44, wherein the light emitted at a range of wavelengths is a wide-band light.

50. The monitor of claim 44, wherein the absorbance spectrum is a wide-band absorbance spectrum.

51. The monitor of claim 44, wherein the multi-linear regression comprises determining a linear combination of the plurality of absorbance spectra of the tissue constituents that best matches the absorbance spectrum.

\* \* \* \* \*